United States Patent [19]
Jensen et al.

[11] Patent Number: 5,891,669
[45] Date of Patent: Apr. 6, 1999

[54] METHODS FOR PRODUCING POLYPEPTIDES IN RESPIRATORY-DEFICIENT CELLS

[75] Inventors: Ejner Bech Jensen, Virum, Denmark; Joel R. Cherry; Susan L. Elrod, both of Davis, Calif.

[73] Assignees: Novo Nordisk A/S, Novoalle,, Bagsvaerd, Denmark; Novo Nordisk Biotech, Davis, Calif.

[21] Appl. No.: 819,458

[22] Filed: Mar. 17, 1997

[51] Int. Cl.⁶ .............................. C12P 21/00; C12N 1/19; C12N 1/21; C12N 9/10

[52] U.S. Cl. ..................... 435/69.1; 435/455; 435/463; 435/183; 435/201; 435/198; 435/190; 435/193; 435/207; 435/208; 435/212; 435/199; 435/219; 435/220; 435/224; 435/225; 435/252.3; 435/254.11; 435/254.21; 435/254.22; 435/254.23; 435/254.3; 435/254.4; 435/254.5

[58] Field of Search ..................... 435/69.1, 6, 172.1, 435/172.3, 183, 320.1, 325, 252.3, 254.11, 254.2, 254.3, 455, 463, 201, 198, 190, 193, 207, 208, 212, 199, 219, 220, 224, 225, 254.21, 254.22, 254.23, 254.4, 254.5

[56] References Cited

U.S. PATENT DOCUMENTS

4,902,620  2/1990  Bard et al. .................................. 435/6

FOREIGN PATENT DOCUMENTS

0 317 209  5/1989  European Pat. Off. .
WO 96/09397  3/1996  WIPO .
WO 97/47736  12/1997  WIPO .
WO 97/47753  12/1997  WIPO .
WO 98/01535  1/1998  WIPO .

OTHER PUBLICATIONS

Schmalix et al., "Kinetics of the Intracellular Avilability of Heme after Supplementing a Heme–Deficient Yeast Mutant with 5–Aminolevulinate".

James E. Bailey, Science, vol. 252, pp. 1668–1675. Jun. 21, 1991.

*Primary Examiner*—David Guzo
*Attorney, Agent, or Firm*—Steve T. Zelson; Elias J. Lambiris; Valeta A. Gregg

[57] ABSTRACT

The present invention relates to methods of producing a polypeptide, comprising: (a) introducing into a respiratory-defective mutant of a cell (i) one or more first nucleic acid sequences which complement the respiratory defect and (ii) a second nucleic acid sequence which encodes the polypeptide; (b) cultivating the cell containing the first and second nucleic acid sequences in a culture medium under aerobic conditions suitable for expression of the first and second nucleic acid sequences; and (c) isolating the polypeptide from the cultivation medium of the cell. The present invention also relates to methods for disrupting a gene in a respiratory-deficient mutant cell. The present invention further relates to respiratory-deficient mutant cells and methods for obtaining such mutant cells.

31 Claims, 11 Drawing Sheets

```
ACCATTGACTCTCAAGCTATGGATCGTGCTCACCGTCTCGGCCAGACAAGACAGGTCACG 60
GTGTATCGCCTGATTACTCGCGGCACCATTGAGGAGCGTATTCGCAAGCGAGCTTTGCAG 120
AAGGAGGAAGTGCAGCGTGTCGTCATCTCAGGTGGCGCAGCTGGTGGGGTTGACTTCAAT 180
ACTCGCAACCGCGAGAGCCGAACCAAGGACATCGCCATGTGGCTGGCAGATGATGAACAG 240
GCGGAGCTTATTGAGCAAAAGGAGAAGGAAGCGCTGGACCGAGGCGAAGTGTTTGGCGCT 300
AGTAAAGGCGGGAAGAAGGCTGCTCAGAAGAGAAAGAGAGATATCACGCTGGATGATATG 360
TATCATGAAGGTATGTGAATCTGATCAAAGCTCTTCGTTCCGGGGAGGCTTCTGGAAATA 420
GTACTAACCGCGTCAATCTATAGGCGAAGGGAACTTTGACGATGCCAGTGCAAAGCCATC 480
AGGAGCGGCCACTCCTGTGTCGACTGCAGAGAATTTAGGCACCCCATCCTCCACGCCAGT 540
TCCTAAACGAGGACGTGGAAGGGGGACAGGAAAGGGCACGTCTAAAAGAGCCAAAACTAC 600
CAAGGAGAGATTACGTCTCATTGATGGCGACGGAGGCTTAGGGCCTAGTTGATTTAATCG 660
ATCTGTGCCTCAATAATGGACACGGCTGGTTATGGTCATGGCGTTCAGAGATTGCATTTC 720
TTTCCCACCCTTTATCTTTCTTTCTTTCCTCTTAAACCCCTCTTTTTTGTTTTTCTTTTT 780
ATCGGACTTTACTTGTGGGCAGCTTACGTTCTGCCTTGTATTAACAGCATATATTCCTGA 840
TTCCTGATGTACGAAGCGATTTAAGAGTCATTGAAGACGAAGGATGAAACCCGTGGTAAT 900
CAGCCGATAATGGCAAAGAGAAGGAGAAGAAAAAAATCAAGTGCGAGTTTTGAAATTGAT 960
GGCAAGATAGACATTGTATCCTGTACCTGTTCTTGGGCTGTGACGGGGGGGGTGAAATTG 1020
ACGGTCATCACCCGGCTATTATTACTATTGTTGTACTGTACATCCGGATCCTGCTGGTCT 1080
GTATCTAGTTAGGGCAATATTCCCCGTCGCCAGGCCTCTTGGGTTATGAATGATTTCATA 1140
GGTGAAGTTTCGTATCCGTACGCACCGAGAGATTTCTTAGTATTACTTGTATTATGAAAA 1200
TGCACTTGCCGAGTTAAGTCCGCCGGCCAATCACGGCGGAGGATATGGTAAGCCGAAAAG 1260
TCTCGCCGAAGTCCCCGACTTACTCTTACTGGAAGTGGCTTAGTGCCCTCAGCGCCCCT 1320
CGCCCTCAGTCCATCAGCCAGATTGACTCTTATTTCTCTCTCCTCTTCGCCGCGGGTGAC 1380
ATATCCCTCTCCTTCTCCCTCTCCCTCTTGACAACATTTCATCTTCGCTTCCTTTTGTGA 1440
TATAGTCAGTTTCGCTATCCATTGAAGCATCACTCATGGAGTCTCTTCTCCAGCAGTCCC 1500
                                     M  E  S  L  L  Q  Q  S
GGGCGATGTGCCCGTTCCTTAAGCGCACATCTCCATCTTCTCTGCGTACGCTGGCAACCG 1560
R  A   M  C  P  F  L   K  R  T  S  P  S  S  L  R  T  L  A  T
CGACTCGACCTAGCACTAGTTCCGGTGGAGGCACTATGTCTAATCTCCAGGTCATTGCCC 1620
 A  T  R  P  S  T  S  S  G  G  G  T  M  S  N  L  Q  V  I  A
GTCGCTGCCCTGTCATGAGCAAGGCTCTGGCCGTGCAGAGCGCTCGCATGGCCGGTACCA 1680
 R   R  C  P  V  M   S  K  A  L  A  V  Q  S  A  R  M  A  G  T
AAAGATTCACCTCATGTGCTGCCGGCATCACCGGTCTCGGCAACAAGCATTGCCGTGCTC 1740
 K  R  F  T  S  C  A  A  G  I  T  G  L  G  N  K  H  C  R  A
CTACTGGGAAGAGAACCCTGCACTCCACCTCCGGTAACGGCGCCAATGTGAGCGCAGAGA 1800
 P  T  G  K  R  T  L  H  S  T  S  G  N  G  ·A  N  V  S  A  E
TCTACAAGAACACCCAGCGAGATCCCGCCGGTTTCTCGAAGATCAAGACCCCTGCCAATG 1860
 I  Y  K  N  T  Q  R  D  P  A  G  F  S  K  ·I  K  T  P  A  N
CTACCGCCGCTGCCGCTACGTCTGGCCCTCGTCCAGAGGCTCCCGTGGCGAAGCCTTTCA 1920
 A  T  A  A  A  A  T  S  G  P  R  P  E  A  P  V  A  K  P  F
ACTACAATTCTTTCTACAACACCGAATTGGAAAAGAAACACAAGGACAAGTCGTATCGCT 1980
 N  Y  N  S  F  Y  N  T  E  L  E  K  K  H  K  D  K  S  Y  R
ATTTCAACAACATCAATCGTCTCGCTCAGGAGTTTCCCCGGGCTCACACCACATCTGCCG 2040
 Y  F  N  N  I  N  R  L  A  Q  E  F  P  R  A  H  T  T  S  A
AGGAACGTGTGACGGTCTGGTGCTCGAACGATTATCTCGGCATGGGCCGCAACCCCGAGG 2100
 E  E  R  V  T  V  W  C  S  N  D  Y  L  G  M  G  R  N  P  E
TTCTGGCCACCATGCATAAGACATTGGACACCTACGGAGCCGGTGCGGGAGGTACTCGCA 2160
 V  L  A  T  M  H  K  T  L  D  T   Y  G  A  G  A  G  G  T  R
ACATTTCAGGTCACAATCAACATGCCGTGAGCCTGGAGAACACCCTGGCCAAATGCACG 2220
  N  I   S  G  H  N  Q  H  A  V  S  L  E  N  T  L  A  K  L  H
GCAAGGAGGCGGCATTAGTCTTCAGCTCATGCTTCGTGGCTAACGATGCCACCCTCGCAA 2280
 G  K  E  A  A  L  V  F  S  S  C  F  V  A  N  D  A  T  L  A
CCCTGGGTAGCAAGTTGCCCGACTGTGTTATTCTGTCCGATAGCCTGAATCATGCATCGA 2340
 T  L  G  S  K  L  P  D  C  V  I  L  S  D  S  L  N  H  A  S
TGATTCAGGGTATTCGCCATTCAGGCGCCAAGAAAATGGTTTTCAAGCATAATGATCTGG 2400
 M  I  Q  G  I  R  H  S  G  A  K  K  M  V  F  K  H  N  D  L
```

FIG. 3A

```
TCGACCTTGAGGCCAAGTTGGCAGCTCTACCTCTTCATGTCCCCAAGATTATTGCATTCG 2460
 V  D  L  E  A  K  L  A  A  L  P  L  H  V  P  K  I  I  A  F
AATCAGTTTATAGCATGTGCGGATCTATTGCCCCAATTGAGAAGATCTGTGATCTTGCAG 2520
 E  S  V  Y  S  M  C  G  S  I  A  P  I  E  K  I  C  D  L  A
ACAAGTACGGTGCCATTACTTTCCTGGATGAAGTCCACGCTGTGGGAATGTACGGACCTC 2580
 D  K  Y  G  A  I  T  F  L  D  E  V  H  A  V  G  M  Y  G  P
ACGGAGCAGGTGTGGCAGAGCACCTTGACTATGACATCTATGCTTCCCAAGATACGGTCA 2640
 H  G  A  G  V  A  E  H  L  D  Y  D  I  Y  A  S  Q  D  T  V
ACCCGCGCAGTACTAAGGGAACCGTGATGGACCGAATCGATATTATCACCGGTACTCTGG 2700
 N  P  R  S  T  K  G  T  V  M  D  R  I  D  I  I  T  G  T  L
GCAAGGCCTACGGATGTGTCGGGGGCTACATTGCTGGATCCGCTGCGATGGTTGACACCA 2760
 G  K* A  Y  G  C  V  G  G  Y  I  A  G  S  A  A  M  V  D  T
TCCGCTCCCTCGCCCCTGGCTTCATCTTCACCACGTCCTTGCCGCCCGCCACCATGGCTG 2820
 I  R  S  L  A  P  G  F  I  F  T  T  S  L  P  P  A  T  M  A
GTGCAGACACTGCTATCCAGTACCAGGCTCGTCACCAGGGCGACCGCGTCCTGCAGCAGT 2880
 G  A  D  T  A  I  Q  Y  Q  A  R  H  Q  G  D  R  V  L  Q  Q
TGCACACCCGCGCGGTCAAAGCAGCTTTCAAGGAGTTGGATATTCCTGTAATTCCCAACC 2940
 L  H  T  R  A  V  K  A  A  F  K  E  L  D  I  P  V  I  P  N
CCTCCCATATCATTCCGCTCCTGGTTGGGGATGCCGAGGTTGCTAAGAAGGCCTCGGACA 3000
 P  S  H  I  I  P  L  L  V  G  D  A  E  V  A  K  K  A  S  D
AGCTTCTGGAGGAGCATGGAATTTATGTACAAGCCATCAACTACCCAACCGTGCCTCGGG 3060
 K  L  L  E  E  H  G  I  Y  V  Q  A  I  N  Y  P  T  V  P  R
GTGAAGAGCGGCTTCGTATCACGCCCACCCCGGGACATATCAAGGAGCACCGCGACCACC 3120
 G  E  E  R  L  R  I  T  P  T  P  G  H  I  K  E  H  R  D  H
TGGTGCAAGCCGTCCAAACAGTCTGGAACGAACTGGGCATCAAACGCACCAGCGATTGGG 3180
 L  V  Q  A  V  Q  T  V  W  N  E  L  G  I  K  R  T  S  D  W
AAGCGCAAGGCGGCTTCGTCGGCGTGGGTGTCGATGGCGCCGAGGCTGAGAACCAGCCGA 3240
 E  A  Q  G  G  F  V  G  V  G  V  D  G  A  E  A  E  N  Q  P
TTTGGAATGATGTGCAGCTGGGGCTGAAGGAAAACGAAGCCATTGAGGCTGCTGTGGAAC 3300
 I  W  N  D  V  Q  L  G  L  K  E  N  E  A  I  E  A  A  V  E
GCGAGTTTGCCGAGGCCCCCATGCGGACCGCCACCCGTCCTGCCGCGGCTGCTGCTTCGT 3360
 R  E  F  A  E  A  P  M  R  T  A  T  R  P  A  A  A  A  S
CAATCCCGGTGGGTGTGGCTGCCTGAAGTGGCTGCCCGCATGTGAGCTGAAATCGACGTG 3420
 S  I  P  V  G  V  A  A  .
GAATTCTATACACACACACACACACACACACACACACACACACACACACACACACACACA 3480
CACACACACACACACACACTAACACACACTATGTTATAAATTCCACATCCACTCCTTTGT 3540
CCCTTGTTGGACGTAATTGGTATTTGGACTATTAGTTAGAACCAGTCAGTCGTTACCATG 3600
TGTTTCGGTTCGACTCGAAATCTGACATGTTGTCTGCCCCATGCCACTTCATCTCCTCC 3660
GTAACCGCAGGGCTTCAAATACACTGCCCAGTAATTGTAGTCAATATAGCAGTTAACTAA 3720
CCTTCACCAATTTCCTAATAACAATAGAAGGGGCCATACACGCAGTACCAAAGATCACCT 3780
ACCTCCGATCAATATCCGAACCTCAGGCTACATACATCAAGTCGCATTAATCGATTCCGA 3840
CCTCTGTTTATCCCTGAAAATAACTAAGATCATGATCTACGTTTGGTAAGTGGGACACCT 3900
ACCTACACTGGGAGGTATTGAATAAAGGCATCATTCATATAGTCACAAGATGCCAGGCC 3960
AATTCATGATATGGATAGCTACTTCCAAACATAATTCAGAGGTATCATTCTGCTCTTCAG 4020
ACAGTTCTTCTCGAAGATCAGTAGGAGCCAGTTTTGACCATTAACTTGTAATGTAATTGC 4080
GATTGTAGTAGATCCGAGATCCATTCACTTTCTAAGGGTTAATTGATTCATTTTACTGAT 4140
ACCTCACCCACCATATT                                            4157
```

```
CTGGACCAATGGTAACCCTCCGTAATTGCCTTACAGATTTAGCCCCAGGGGGGTTATGGTATCCTTGGGTA         70
TTGAGGCCTGGAAATTTTTTAGCCACCAGTTTACAGCCAGTTTCCGTTTGTAAATATTTCACATCCCCC          140
GACCCTGTCCCAATACAATAATTTTTCGCTATACGCCCCCTAGCGTTGTTTATGATCCTTAAAT              210
CCTTACTTGTACCTGAAAATTGCAACAAATGTACTGACCTGGCCATTTATATCATTGCCCTG                280
CGAAGTCGTATTCTGCCAGTGGCACAGGCGCTATTCTCTTTCTCCCTCCACCGCGTTTCTATCTTCCA          350
TAGCACCCCACTTGCTTGCCGCTCCTGTCATTATGTCCTTTTCTAATCTCGTCTCTGACCTGCCCTTCAG        420
                   M  S  F  S  N  L  V  S  Q  L  A  F  R
AGATTCTCATGATGACCGAAGTTCTCAGATATCTCAGGTACAATCGCAAGCCACTGCACGATCGTATACA        490
 D  S  H  D  D  R  S  S  Q  I  S  Q  V  Q  S  Q  A  T  A  R  S  Y  T
AGCACAGCTGCCACAAGCGTCAGCAGATATCTCAAGCTTCATTCCGGTTACAGCCATC                    560
 S  T  A  A  T  S  V  S  I  S  Q  D  I  S  S  Q  L  H  S  G  Y  S  H
CACTGAGCCGATCATGGCAGGCTGAAAGACAGTTGACTAAAGTCCGCATTTCTTTTGTATTTACTGAGC         630
 P  L  S  R  S  W  Q  A  E  R  Q  L  T  K
TGCTCTAACCCCGAGATAGGAGAAATGCTTATTTATCCTCTCTTCATCACCGATAATCCCGATGAGGAGACT      700
         E  M  L  I  Y  P  L  F  I  T  D  N  P  D  E  E  T
CCTATCCCCGTCTCTCCCTGGACAGTATCGTCGAGGATTAAACCGTCTAGTTCCTTTCATCAAACCACTTG       770
 P  I  P  S  L  P  G  Q  Y  R  R  G  L  N  R  L  V  P  F  I  K  P  L
CCCACAAGGGCTACGCTCAGTCATCCTGTTTGGCGTCCCACTACACCCCTCTGCGAAGGATGCACTAGG         840
 A  H  K  G  L  R  S  V  I  L  F  G  V  P  L  H  P  S  A  K  D  A  L  G
TACCGCTGCAGACGATCCATCTGACCCGGTAATTCAAGCTATTGCTTAGGTCGCGGTTTCCTCAA             910
 T  A  A  D  D  P  S  G  P  V  I  Q  A  I  R  L  L  R  S  R  F  P  Q
```

```
AAATTGATGGCAAGATAGACATTGTATCCTGTACCTGTTCTTGGGCTGTGACGGGGGGTGAAATTGACGGTCATCACCCGGCTATTAT     90
TACTATTGTTGTACTGTGTACATCCGGATCCTGCTGGTCTGTATCTAGTTAGGCAATATTCCCGTGCCAGGCCTCTTGGGTTATGAATG    180
ATTTCATAGGTGAAGTTTCGTATCCGTACGCCACCGAGAGATTTCTTAGTATTACTTGTATTATGAAAATGCACTTGCCGAGTTAAGTCCG    270
CCGGCCAATCACGGCGGAGGATATGGTAAGCCGAAAAGTCTCGACTTACTCTTACTGGAAGTGGCTTAGTGCCCTCAG    360
CGCCCCCTCGCCCTCAGTCCATCAGCCAGATTGACTCTTATTTCTCGCCGGGTGACATATCCCTCTTCCCTCT    450
CCCTCTTGACAACATTTCATCTTCGCTTCCTTTTGTGATATAGTCAGTTTCGTATCCATTGAAGCATCACTCATGGAGTCTCTTCTCCA    540
                                                                         M  E  S  L  L  Q      
GCAGTCCCGGGCGATGCCCGTTCCTTAAGGCGCACATCTCCATCTTCTCTGGCTGGCAACCGCGACTCGACCTAGCACTAGTTC    630
 Q  S  R  A  M  C  P  F  L  K  R  T  S  P  S  S  L  R  T  L  A  T  R  P  S  T  S  S
CGGTGGAGGCACTATGTCTAATCTCCAGGTCATTGCCCGTCATGAGCAAGGCTCTGGCCGTGCAGAGCCCAAATTGCAC    720
 G  G  T  M  S  N  L  Q  V  I  A  R  R  C  P  V  M  S  K  A  L  A  V  Q  SΔP  N  C  T
GGCAAGGAGGGCATTAGTCTTCAGCTCATGCTGGCTAACGATGCCAACCCTGGGTAGCAACCCTGGGTAGCAAGTTGCCCGACTGTGTT    810
 A  R  R  H  .  S  S  A  H  A  S  W  L  T  M  P  P  S  Q  P  W  V  A  S  C  P  T  V  L
ATTCTGTCCGATAGCCTGAATCATGCATCGATGATTCAGGGTATTCGCCATTCAGGCGCCAAGAAAATGGTTTTCAAGCATAATGATCTG    900
 A  R  R  H  .  S  S  A  H  A  S  W  L  T  M  P  P  S  Q  P  W  V  A  S  C  P  T  V  L
GTCGACCTTGAGGCCAAGTTGGCAGCTCTACCTCTTCATGTCCCAAGATTATTGCATTCAGTTTATAGCATGTGCGGATCTATT    990
 F  C  P  I  A  .  I  M  H  R  .  F  R  V  F  A  I  Q  A  P  R  K  W  F  S  S  I  M  I  W
GCCCCAATTGAGAAGATCTGTGATCTTGCAGACAAGTACGGTGCCATTACTTTCCTGGATGAAGTCCACGCTGTGGGAATGTACGGACCT    1080
 S  T  L  R  P  S  W  Q  L  Y  L  F  M  S  P  R  L  L  H  S  N  Q  F  I  A  C  A  D  L  L
 P  Q  L  R  R  S  V  I  L  Q  T  S  T  V  P  L  L  S  W  M  K  S  T  L  W  E  C  T  D  L
```

```
CACGGAGCAGGTGTGGCAGAGCACCTTGACTATGACATCTATGCTTCCAAGATACGGTCAACCCGCGCAGTACTAAGGGAACCGTGATG  1170
  T  E  Q  V  W  Q  S  T  L  T  M  T  S  M  L  P  K  I  R  S  T  R  A  V  L  R  E  P     W
GACCGAATCGATATTATCACCGTACTCTGGGCAAGGCCTACGGATGTGTCGGGGGCTACATTGCTGGATCCGCTGGATGGTTGACACC    1260
  T  E  Q  I  D  I  I  T  V  L  W  A  R  P  T  D  V  S  G  A  T  L  D  P  L  R  W  L  T  P
ATCCGGCTCCCTGCCCCTGGCTTCATCTTCACCAGTCCTTGCCGCCCACCATGGCTGCAGACACTGCTATCCAGTACCAGGCT         1350
  T  E  S  I  L  S  P  V  L  W  A  R  P  T  D  V  S  G  A  T  L  D  P  L  R  W  L  T  P
CGTCACCAGGGCGACCGCGTCCTGCAGCAGTTGCACACCCGGGTCAAAGCAGTTTCAAGGAGTTGGATATTCCTGTAATTCCCAAC      1440
  S  A  P  S  P  L  A  S  S  P  R  P  C  R  P  P  P  W  L  V  Q  T  L  L  S  S  T  R  L
CCCTCCCATATCATTCCGCTCCTTGGTTGGGGATGCCGAGGTTGCTAAGAAGGCCTCGGACAAGCTTCTGGAGGAGCATGGAATTTATGTA 1530
  V  T  R  A  T  A  S  C  S  S  C  T  P  A  R  S  K  Q  L  S  R  S  W  I  F  L  F  P  T
CAAGCCATCAACTACCCAACCCGTCAAACAGTCTGGAACAGTGGGCATCAACGCGATTGGGAAGCGCAAGGCGATTGGGCTGAAGAGCACCGCGACCAC 1620
  P  P  I  S  F  R  S  W  L  G  M  P  R  L  L  R  R  P  R  T  S  F  W  R  S  M  E  F  M  Y
CTGGTGCAAGCCGTCAAACAGTCTGGAACAGTGGGCATCAACGCGATTGGGAAGCGCAAGGCGATTGGGCTGAAGAGCACCGCGACCAC  1710
  K  P  S  T  Q  P  C  L  G  V  K  S  G  F  V  S  R  P  P  R  D  I  S  R  S  T  A  T  T
CTGGTGCAAGCCGTCAAACAGTCTGGAACAGTCTGGAACGCGATCAACGCGATTGGGCTGAAAGGAAAACGAAGCCATTGAGGCTGTGTGGAA         1800
  W  C  K  P  S  K  Q  S  G  T  N  W  A  S  N  A  P  A  I  G  K  R  K  A  A  S  S  A  W  V
GTCGATGGCCCGAGGCTGAGAACCAGCCCATGCGCACCCCGTCCTGCCGGCGGTGCTGCTTCGTCAATCCCGGTTGGGTGGCCTGCCTGAAGT  1890
  S  M  A  P  R  L  R  T  S  R  F  G  M  M  C  S  W  G  .  R  K  T  K  P  L  R  L  L  W  N
CGCGAGTTTGCCGAGGCCCATGCGCACCCCGTCCTGCCGGCGGTGCTGCTTCGTCAATCCCGGTTGGGTGGCCTGCCTGAAGT
  A  S  L  P  R  P  P  C  G  P  P  P  V  L  P  R  L  L  R  Q  S  R  W  V  W  L  P
GGCTGCCCGCATGTGAGCTGAAATCGACGTGGAATT 1926
```

FIG. 8B

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 4157 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ACCATTGACT   CTCAAGCTAT   GGATCGTGCT   CACCGTCTCG   GCCAGACAAG   ACAGGTCACG        60
```

```
GTGTATCGCC  TGATTACTCG  CGGCACCATT  GAGGAGCGTA  TTCGCAAGCG  AGCTTTGCAG    120
AAGGAGGAAG  TGCAGCGTGT  CGTCATCTCA  GGTGGCGCAG  CTGGTGGGGT  TGACTTCAAT    180
ACTCGCAACC  GCGAGAGCCG  AACCAAGGAC  ATCGCCATGT  GGCTGGCAGA  TGATGAACAG    240
GCGGAGCTTA  TTGAGCAAAA  GGAGAAGGAA  GCGCTGGACC  GAGGCGAAGT  GTTTGGCGCT    300
AGTAAAGGCG  GAAGAAGGC   TGCTCAGAAG  AGAAGAGAG   ATATCACGCT  GGATGATATG    360
TATCATGAAG  GTATGTGAAT  CTGATCAAAG  CTCTTCGTTC  CGGGGAGGCT  TCTGGAAATA    420
GTACTAACCG  CGTCAATCTA  TAGGCGAAGG  GAACTTTGAC  GATGCCAGTG  CAAAGCCATC    480
AGGAGCGGCC  ACTCCTGTGT  CGACTGCAGA  GAATTTAGGC  ACCCCATCCT  CCACGCCAGT    540
TCCTAAACGA  GGACGTGGAA  GGGGACAGG   AAAGGGCACG  TCTAAAAGAG  CCAAAACTAC    600
CAAGGAGAGA  TTACGTCTCA  TTGATGGCGA  CGGAGGCTTA  GGGCCTAGTT  GATTTAATCG    660
ATCTGTGCCT  CAATAATGGA  CACGGCTGGT  TATGGTCATG  GCGTTCAGAG  ATTGCATTTC    720
TTTCCCACCC  TTTATCTTTC  TTTCTTTCCT  CTTAAACCCC  TCTTTTTTGT  TTTTCTTTTT    780
ATCGGACTTT  ACTTGTGGGC  AGCTTACGTT  CTGCCTTGTA  TTAACAGCAT  ATATTCCTGA    840
TTCCTGATGT  ACGAAGCGAT  TTAAGAGTCA  TTGAAGACGA  AGGATGAAAC  CCGTGGTAAT    900
CAGCCGATAA  TGGCAAAGAG  AAGGAGAAGA  AAAAAATCAA  GTGCGAGTTT  TGAAATTGAT    960
GGCAAGATAG  ACATTGTATC  CTGTACCTGT  TCTTGGGCTG  TGACGGGGGG  GGTGAAATTG   1020
ACGGTCATCA  CCCGGCTATT  ATTACTATTG  TTGTACTGTA  CATCCGGATC  CTGCTGGTCT   1080
GTATCTAGTT  AGGGCAATAT  TCCCCGTCGC  CAGGCCTCTT  GGGTTATGAA  TGATTTCATA   1140
GGTGAAGTTT  CGTATCCGTA  CGCACCGAGA  GATTTCTTAG  TATTACTTGT  ATTATGAAAA   1200
TGCACTTGCC  GAGTTAAGTC  CGCCGGCCAA  TCACGGCGGA  GGATATGGTA  AGCCGAAAAG   1260
TCTCGCCGAA  GTCCCCGACT  TACTCTTACT  GGAAGTGGCT  TAGTGCCCTC  AGCGCCCCCT   1320
CGCCCTCAGT  CCATCAGCCA  GATTGACTCT  TATTTCTCTC  TCCTCTTCGC  CGCGGGTGAC   1380
ATATCCCTCT  CCTTCTCCCT  CTCCCTCTTG  ACAACATTTC  ATCTTCGCTT  CCTTTTGTGA   1440
TATAGTCAGT  TTCGCTATCC  ATTGAAGCAT  CACTCATGGA  GTCTCTTCTC  CAGCAGTCCC   1500
GGGCGATGTG  CCCGTTCCTT  AAGCGCACAT  CTCCATCTTC  TCTGCGTACG  CTGGCAACCG   1560
CGACTCGACC  TAGCACTAGT  TCCGGTGGAG  GCACTATGTC  TAATCTCCAG  GTCATTGCCC   1620
GTCGCTGCCC  TGTCATGAGC  AAGGCTCTGG  CCGTGCAGAG  CGCTCGCATG  GCCGGTACCA   1680
AAAGATTCAC  CTCATGTGCT  GCCGGCATCA  CCGGTCTCGG  CAACAAGCAT  TGCCGTGCTC   1740
CTACTGGGAA  GAGAACCCTG  CACTCCACCT  CCGGTAACGG  CGCCAATGTG  AGCGCAGAGA   1800
TCTACAAGAA  CACCCAGCGA  GATCCCGCCG  GTTTCTCGAA  GATCAAGACC  CCTGCCAATG   1860
CTACCGCCGC  TGCCGCTACG  TCTGGCCCTC  GTCCAGAGGC  TCCCGTGGCG  AAGCCTTTCA   1920
ACTACAATTC  TTTCTACAAC  ACCGAATTGG  AAAAGAAACA  CAAGGACAAG  TCGTATCGCT   1980
ATTTCAACAA  CATCAATCGT  CTCGCTCAGG  AGTTTCCCCG  GGCTCACACC  ACATCTGCCG   2040
AGGAACGTGT  GACGGTCTGG  TGCTCGAACG  ATTATCTCGG  CATGGGCCGC  AACCCCGAGG   2100
TTCTGGCCAC  CATGCATAAG  ACATTGGACA  CCTACGGAGC  CGGTGCGGGA  GGTACTCGCA   2160
ACATTTCAGG  TCACAATCAA  CATGCCGTGA  GCCTGGAGAA  CACCCTGGCC  AAATTGCACG   2220
GCAAGGAGGC  GGCATTAGTC  TTCAGCTCAT  GCTTCGTGGC  TAACGATGCC  ACCCTCGCAA   2280
CCCTGGGTAG  CAAGTTGCCC  GACTGTGTTA  TTCTGTCCGA  TAGCCTGAAT  CATGCATCGA   2340
TGATTCAGGG  TATTCGCCAT  TCAGGCGCCA  AGAAAATGGT  TTTCAAGCAT  AATGATCTGG   2400
TCGACCTTGA  GGCCAAGTTG  GCAGCTCTAC  CTCTTCATGT  CCCCAAGATT  ATTGCATTCG   2460
```

-continued

| | | | | | |
|---|---|---|---|---|---|
|AATCAGTTTA|TAGCATGTGC|GGATCTATTG|CCCCAATTGA|GAAGATCTGT|GATCTTGCAG|2520|
|ACAAGTACGG|TGCCATTACT|TTCCTGGATG|AAGTCCACGC|TGTGGGAATG|TACGGACCTC|2580|
|ACGGAGCAGG|TGTGGCAGAG|CACCTTGACT|ATGACATCTA|TGCTTCCCAA|GATACGGTCA|2640|
|ACCCGCGCAG|TACTAAGGGA|ACCGTGATGG|ACCGAATCGA|TATTATCACC|GGTACTCTGG|2700|
|GCAAGGCCTA|CGGATGTGTC|GGGGGCTACA|TTGCTGGATC|CGCTGCGATG|GTTGACACCA|2760|
|TCCGCTCCCT|CGCCCCTGGC|TTCATCTTCA|CCACGTCCTT|GCCGCCCGCC|ACCATGGCTG|2820|
|GTGCAGACAC|TGCTATCCAG|TACCAGGCTC|GTCACCAGGG|CGACCGCGTC|CTGCAGCAGT|2880|
|TGCACACCCG|CGCGGTCAAA|GCAGCTTTCA|AGGAGTTGGA|TATTCCTGTA|ATTCCCAACC|2940|
|CCTCCCATAT|CATTCCGCTC|CTGGTTGGGG|ATGCCGAGGT|TGCTAAGAAG|CCTCGGACA|3000|
|AGCTTCTGGA|GGAGCATGGA|ATTTATGTAC|AAGCCATCAA|CTACCCAACC|GTGCCTCGGG|3060|
|GTGAAGAGCG|GCTTCGTATC|ACGCCCACCC|CGGGACATAT|CAAGGAGCAC|CGCGACCACC|3120|
|TGGTGCAAGC|CGTCCAAACA|GTCTGGAACG|AACTGGGCAT|CAAACGCACC|AGCGATTGGG|3180|
|AAGCGCAAGG|CGGCTTCGTC|GGCGTGGGTG|TCGATGGCGC|CGAGGCTGAG|AACCAGCCGA|3240|
|TTTGGAATGA|TGTGCAGCTG|GGGCTGAAGG|AAAACGAAGC|CATTGAGGCT|GCTGTGGAAC|3300|
|GCGAGTTTGC|CGAGGCCCCC|ATGCGGACCG|CCACCCGTCC|TGCCGCGGCT|GCTGCTTCGT|3360|
|CAATCCCGGT|GGGTGTGGCT|GCCTGAAGTG|GCTGCCCGCA|TGTGAGCTGA|AATCGACGTG|3420|
|GAATTCTATA|CACACACACA|CACACACACA|CACACACACA|CACACACACA|CACACACACA|3480|
|CACACACACA|CACACACACT|AACACACACT|ATGTTATAAA|TTCCACATCC|ACTCCTTTGT|3540|
|CCCTTGTTGG|ACGTAATTGG|TATTTGGACT|ATTAGTTAGA|ACCAGTCAGT|CGTTACCATG|3600|
|TGTTTCGGTT|CGACTCGAAA|TCTGACATGT|TGTCTGCCCC|CATGCCACTT|CATCTCCTCC|3660|
|GTAACCGCAG|GGCTTCAAAT|ACACTGCCCA|GTAATTGTAG|TCAATATAGC|AGTTAACTAA|3720|
|CCTTCACCAA|TTTCCTAATA|ACAATAGAAG|GGGCCATACA|CGCAGTACCA|AAGATCACCT|3780|
|ACCTCCGATC|AATATCCGAA|CCTCAGGCTA|CATACATCAA|GTCGCATTAA|TCGATTCCGA|3840|
|CCTCTGTTTA|TCCCTGAAAA|TAACTAAGAT|CATGATCTAC|GTTTGGTAAG|TGGGACACCT|3900|
|ACCTACACTG|GGAGGTATTG|AATAAAGGCA|TCATTCATAT|AGTCACAAGA|TGCCAGGGCC|3960|
|AATTCATGAT|ATGGATAGCT|ACTTCCAAAC|ATAATTCAGA|GGTATCATTC|TGCTCTTCAG|4020|
|ACAGTTCTTC|TCGAAGATCA|GTAGGAGCCA|GTTTTGACCA|TTAACTTGTA|ATGTAATTGC|4080|
|GATTGTAGTA|GATCCAGAGAT|CCATTCACTT|TCTAAGGGTT|AATTGATTCA|TTTTACTGAT|4140|
|ACCTCACCCA|CCATATT| | | | |4157|

( 2 ) INFORMATION FOR SEQ ID NO:2:

( i ) SEQUENCE CHARACTERISTICS:
    ( A ) LENGTH: 636 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Met  Glu  Ser  Leu  Leu  Gln  Gln  Ser  Arg  Ala  Met  Cys  Pro  Phe  Leu  Lys
 1                  5                        10                         15

Arg  Thr  Ser  Pro  Ser  Ser  Leu  Arg  Thr  Leu  Ala  Thr  Ala  Thr  Arg  Pro
               20                       25                       30

Ser  Thr  Ser  Ser  Gly  Gly  Gly  Thr  Met  Ser  Asn  Leu  Gln  Val  Ile  Ala
          35                       40                       45
```

```
Arg  Arg  Cys  Pro  Val  Met  Ser  Lys  Ala  Leu  Ala  Val  Gln  Ser  Ala  Arg
     50                  55                      60

Met  Ala  Gly  Thr  Lys  Arg  Phe  Thr  Ser  Cys  Ala  Ala  Gly  Ile  Thr  Gly
65                       70                  75                           80

Leu  Gly  Asn  Lys  His  Cys  Arg  Ala  Pro  Thr  Gly  Lys  Arg  Thr  Leu  His
               85                      90                           95

Ser  Thr  Ser  Gly  Asn  Gly  Ala  Asn  Val  Ser  Ala  Glu  Ile  Tyr  Lys  Asn
               100                 105                           110

Thr  Gln  Arg  Asp  Pro  Ala  Gly  Phe  Ser  Lys  Ile  Lys  Thr  Pro  Ala  Asn
          115                 120                      125

Ala  Thr  Ala  Ala  Ala  Ala  Thr  Ser  Gly  Pro  Arg  Pro  Glu  Ala  Pro  Val
     130                 135                      140

Ala  Lys  Pro  Phe  Asn  Tyr  Asn  Ser  Phe  Tyr  Asn  Thr  Glu  Leu  Glu  Lys
145                      150                 155                           160

Lys  His  Lys  Asp  Lys  Ser  Tyr  Arg  Tyr  Phe  Asn  Asn  Ile  Asn  Arg  Leu
               165                      170                           175

Ala  Gln  Glu  Phe  Pro  Arg  Ala  His  Thr  Thr  Ser  Ala  Glu  Glu  Arg  Val
               180                      185                      190

Thr  Val  Trp  Cys  Ser  Asn  Asp  Tyr  Leu  Gly  Met  Gly  Arg  Asn  Pro  Glu
          195                      200                 205

Val  Leu  Ala  Thr  Met  His  Lys  Thr  Leu  Asp  Thr  Tyr  Gly  Ala  Gly  Ala
     210                 215                      220

Gly  Gly  Thr  Arg  Asn  Ile  Ser  Gly  His  Asn  Gln  His  Ala  Val  Ser  Leu
225                      230                 235                           240

Glu  Asn  Thr  Leu  Ala  Lys  Leu  His  Gly  Lys  Glu  Ala  Ala  Leu  Val  Phe
               245                      250                           255

Ser  Ser  Cys  Phe  Val  Ala  Asn  Asp  Ala  Thr  Leu  Ala  Thr  Leu  Gly  Ser
               260                 265                      270

Lys  Leu  Pro  Asp  Cys  Val  Ile  Leu  Ser  Asp  Ser  Leu  Asn  His  Ala  Ser
          275                      280                 285

Met  Ile  Gln  Gly  Ile  Arg  His  Ser  Gly  Ala  Lys  Lys  Met  Val  Phe  Lys
     290                 295                      300

His  Asn  Asp  Leu  Val  Asp  Leu  Glu  Ala  Lys  Leu  Ala  Ala  Leu  Pro  Leu
305                      310                 315                           320

His  Val  Pro  Lys  Ile  Ile  Ala  Phe  Glu  Ser  Val  Tyr  Ser  Met  Cys  Gly
               325                      330                           335

Ser  Ile  Ala  Pro  Ile  Glu  Lys  Ile  Cys  Asp  Leu  Ala  Asp  Lys  Tyr  Gly
               340                      345                      350

Ala  Ile  Thr  Phe  Leu  Asp  Glu  Val  His  Ala  Val  Gly  Met  Tyr  Gly  Pro
          355                      360                      365

His  Gly  Ala  Gly  Val  Ala  Glu  His  Leu  Asp  Tyr  Asp  Ile  Tyr  Ala  Ser
     370                 375                      380

Gln  Asp  Thr  Val  Asn  Pro  Arg  Ser  Thr  Lys  Gly  Thr  Val  Met  Asp  Arg
385                      390                      395                      400

Ile  Asp  Ile  Ile  Thr  Gly  Thr  Leu  Gly  Lys  Ala  Tyr  Gly  Cys  Val  Gly
               405                      410                           415

Gly  Tyr  Ile  Ala  Gly  Ser  Ala  Ala  Met  Val  Asp  Thr  Ile  Arg  Ser  Leu
               420                 425                      430

Ala  Pro  Gly  Phe  Ile  Phe  Thr  Thr  Ser  Leu  Pro  Pro  Ala  Thr  Met  Ala
          435                      440                      445

Gly  Ala  Asp  Thr  Ala  Ile  Gln  Tyr  Gln  Ala  Arg  His  Gln  Gly  Asp  Arg
     450                 455                      460

Val  Leu  Gln  Gln  Leu  His  Thr  Arg  Ala  Val  Lys  Ala  Ala  Phe  Lys  Glu
```

|     |     |     |     | 465 |     |     |     | 470 |     |     |     | 475 |     |     |     | 480 |
|-----|-----|-----|-----|-----|-----|-----|-----|-----|-----|-----|-----|-----|-----|-----|-----|-----|

Leu Asp Ile Pro Val Ile Pro Asn Pro Ser His Ile Ile Pro Leu Leu
            485                 490                 495

Val Gly Asp Ala Glu Val Ala Lys Lys Ala Ser Asp Lys Leu Leu Glu
            500                 505                 510

Glu His Gly Ile Tyr Val Gln Ala Ile Asn Tyr Pro Thr Val Pro Arg
            515                 520                 525

Gly Glu Glu Arg Leu Arg Ile Thr Pro Thr Pro Gly His Ile Lys Glu
             530                 535                 540

His Arg Asp His Leu Val Gln Ala Val Gln Thr Val Trp Asn Glu Leu
545                 550                 555                 560

Gly Ile Lys Arg Thr Ser Asp Trp Glu Ala Gln Gly Gly Phe Val Gly
                565                 570                 575

Val Gly Val Asp Gly Ala Glu Ala Glu Asn Gln Pro Ile Trp Asn Asp
            580                 585                 590

Val Gln Leu Gly Leu Lys Glu Asn Glu Ala Ile Glu Ala Ala Val Glu
            595                 600                 605

Arg Glu Phe Ala Glu Ala Pro Met Arg Thr Ala Thr Arg Pro Ala Ala
    610                 615                 620

Ala Ala Ala Ser Ser Ile Pro Val Gly Val Ala Ala
625                 630                 635

(2) INFORMATION FOR SEQ ID NO:3:

(i) SEQUENCE CHARACTERISTICS:
        (A) LENGTH: 1807 base pairs
        (B) TYPE: nucleic acid
        (C) STRANDEDNESS: single
        (D) TOPOLOGY: linear (xi) SEQUENCE DESCRIPTION: SEQ ID NO:3:

```
CTGGACCAAT  GGTAACCCTC  CGTAATTGCC  TTACAGATTT  AGCCCAGGGG  GGTTATGGTA    60

TCCTTGGGTA  TTGAGGCCTG  GAAATTTTTT  TAGCCACCAG  TTTACAGCCA  GTTTCCGTTT   120

GTAAATATTT  CACATCCCCC  GACCCTGTCC  CAATACAATA  ATTTTTTCGC  TATATATAAC   180

GCCCCTAGCG  TTGTTTTATG  ATCCTTAAAT  CCTTACTTGT  ACCTGAAAAT  TGCAACAAAT   240

GTACTGACCT  GGATCGCTGG  CCATTTATAT  CATTGCCCTG  CGAAGTCGTA  TTCTGCCAGT   300

GGCACAGGCG  CTATTCTCTT  TTCTTCCCTC  CACCGCGTTT  CTATCTTCCA  TAGCACCCCA   360

CTTGCTTGCC  GCTCCTGTCA  TTATGTCCTT  TTCTAATCTC  GTCTCTGACC  TCGCCTTCAG   420

AGATTCTCAT  GATGACCGAA  GTTCTCAGAT  ATCTCAGGTA  CAATCGCAAG  CCACTGCACG   480

ATCGTATACA  AGCACAGCTG  CCACAAGCGT  CAGCATATCT  GGCGACATCT  CAAGCCAGCT   540

TCATTCCGGT  TACAGCCATC  CACTGAGCCG  ATCATGGCAG  GCTGAAAGAC  AGTTGACTAA   600

AGTCCGCATT  TTCTTTTGTA  TTTACTGAGC  TGCTCTAACC  CCGAGATAGG  AAATGCTTAT   660

TTATCCTCTC  TTCATCACCG  ATAATCCCGA  TGAGGAGACT  CCTATCCCGT  CTCTCCCTGG   720

ACAGTATCGT  CGAGGATTAA  ACCGTCTAGT  TCCTTTCATC  AAACCACTTG  CCCACAAGGG   780

GCTACGCTCA  GTCATCCTGT  TTGGCGTCCC  ACTACACCCC  TCTGCGAAGG  ATGCACTAGG   840

TACCGCTGCA  GACGATCCAT  CTGGACCGGT  AATTCAAGCT  ATTCGCTTGC  TTAGGTCGCG   900

GTTTCCTCAA  CTTTATATCG  TGACAGATGT  GTGCCTTTGC  GAGTATACTT  CGCATGGCCA   960

CTGTGGGATA  CTGCGAGAAG  ATGGGACTCT  TGATAATACA  CAGTCTGTGG  ATCGGATTTC  1020

GGATGTTGCT  CTGGCTTATG  CTGCCGCCGG  AGCCCATTGT  GTCGCTCCGT  CTGATATGAA  1080

TGATGGGCGA  GTGCGTGCTA  TAAAACTGAA  GCTTATTGAA  GCCGGGATGG  CCCACCGTGT  1140
```

```
CCTACTGATG  TCCTACAGCG  CCAAATTTAG  CGGTTGTTTG  TACGGCCCTT  TCCGTGATGC   1200

AGCGGGGTCC  TGCCCATCAT  TCGGGGATCG  CAGATGCTAC  CAGTTACCAC  CCGGAGGCCG   1260

TGGACTTGCT  CGGCGCGCTA  TACAGAGAGA  TATAGGCGAA  GGGGCAGACA  TCATAATGGT   1320

AAAGCCGGCG  AGCAGCTACC  TGGACATTAT  CAGAGACGCA  AAAGAAATTG  CCAAAGACAT   1380

TCCCATTGCT  GCTTACCAGG  TCAGCGGTGA  GTATGCTATG  ATACATGCTG  GTGCCAAGGC   1440

GGGCGTATTT  GACTTGAAAT  CCATGGCCTT  TGAAAGTACT  GAAGGGATTA  TAAGGGCTGG   1500

TGCTGGGATT  ATAGTAAGCT  ATTTCGTGCC  TGATTTTCTA  GATTGGCTTT  CGAAATGATT   1560

TAGCTAGATG  GAGCGTGATG  AAAGCATCCA  CCAGATAAAT  AGCAGTGACG  ATCGCGTTTG   1620

AATCATACCT  ATTGGAGTAG  AAGTCTCGGT  ATCTCGTTGG  GGATTCTCTA  GGTTGCTTAT   1680

TTAACGTAAT  GCCACGCCAT  GTGTTATATA  TTGCCTAAAT  ACTTTTATAA  AAGATACACC   1740

AAGCTGATGG  TGCCAAGTGA  CCACTTCTAA  TAAATACAAT  TATACCAATT  CCTCCGAAAT   1800

ATGCGGG                                                                 1807
```

( 2 ) INFORMATION FOR SEQ ID NO:4:

( i ) SEQUENCE CHARACTERISTICS:
        ( A ) LENGTH: 375 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met  Ser  Phe  Ser  Asn  Leu  Val  Ser  Asp  Leu  Ala  Phe  Arg  Asp  Ser  His
 1              5                        10                       15

Asp  Asp  Arg  Ser  Ser  Gln  Ile  Ser  Gln  Val  Gln  Ser  Gln  Ala  Thr  Ala
               20                        25                       30

Arg  Ser  Tyr  Thr  Ser  Thr  Ala  Ala  Thr  Ser  Val  Ser  Ile  Ser  Gly  Asp
                    35                        40                       45

Ile  Ser  Ser  Gln  Leu  His  Ser  Gly  Tyr  Ser  His  Pro  Leu  Ser  Arg  Ser
     50                        55                        60

Trp  Gln  Ala  Glu  Arg  Gln  Leu  Thr  Lys  Glu  Met  Leu  Ile  Tyr  Pro  Leu
65                       70                        75                       80

Phe  Ile  Thr  Asp  Asn  Pro  Asp  Glu  Glu  Thr  Pro  Ile  Pro  Ser  Leu  Pro
                         85                        90                       95

Gly  Gln  Tyr  Arg  Arg  Gly  Leu  Asn  Arg  Leu  Val  Pro  Phe  Ile  Lys  Pro
                    100                       105                      110

Leu  Ala  His  Lys  Gly  Leu  Arg  Ser  Val  Ile  Leu  Phe  Gly  Val  Pro  Leu
               115                       120                      125

His  Pro  Ser  Ala  Lys  Asp  Ala  Leu  Gly  Thr  Ala  Ala  Asp  Asp  Pro  Ser
     130                       135                      140

Gly  Pro  Val  Ile  Gln  Ala  Ile  Arg  Leu  Leu  Arg  Ser  Arg  Phe  Pro  Gln
145                      150                       155                      160

Leu  Tyr  Ile  Val  Thr  Asp  Val  Cys  Leu  Cys  Glu  Tyr  Thr  Ser  His  Gly
                         165                       170                      175

His  Cys  Gly  Ile  Leu  Arg  Glu  Asp  Gly  Thr  Leu  Asp  Asn  Thr  Gln  Ser
                    180                       185                      190

Val  Asp  Arg  Ile  Ser  Asp  Val  Ala  Leu  Ala  Tyr  Ala  Ala  Ala  Gly  Ala
               195                       200                      205

His  Cys  Val  Ala  Pro  Ser  Asp  Met  Asn  Asp  Gly  Arg  Val  Arg  Ala  Ile
     210                       215                      220
```

| | | | | | | | | | | | | | | |
|---|---|---|---|---|---|---|---|---|---|---|---|---|---|---|
| Lys 225 | Leu | Lys | Leu | Ile | Glu 230 | Ala | Gly | Met | Ala | His 235 | Arg | Val | Leu | Leu 240 | Met |
| Ser | Tyr | Ser | Ala | Lys 245 | Phe | Ser | Gly | Cys | Leu 250 | Tyr | Gly | Pro | Phe | Arg 255 | Asp |
| Ala | Ala | Gly | Ser 260 | Cys | Pro | Ser | Phe | Gly 265 | Asp | Arg | Arg | Cys | Tyr 270 | Gln | Leu |
| Pro | Pro | Gly 275 | Gly | Arg | Gly | Leu | Ala 280 | Arg | Arg | Ala | Ile | Gln 285 | Arg | Asp | Ile |
| Gly | Glu 290 | Gly | Ala | Asp | Ile | Ile 295 | Met | Val | Lys | Pro | Ala 300 | Ser | Ser | Tyr | Leu |
| Asp 305 | Ile | Ile | Arg | Asp | Ala 310 | Lys | Glu | Ile | Ala | Lys 315 | Asp | Ile | Pro | Ile | Ala 320 |
| Ala | Tyr | Gln | Val | Ser 325 | Gly | Glu | Tyr | Ala | Met 330 | Ile | His | Ala | Gly | Ala 335 | Lys |
| Ala | Gly | Val | Phe 340 | Asp | Leu | Lys | Ser | Met 345 | Ala | Phe | Glu | Ser | Thr 350 | Glu | Gly |
| Ile | Ile | Arg 355 | Ala | Gly | Ala | Gly | Ile 360 | Ile | Val | Ser | Tyr | Phe 365 | Val | Pro | Asp |
| Phe | Leu 370 | Asp | Trp | Leu | Ser | Lys 375 | | | | | | | | | |

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTTATGATGG AGGCCCTTCT CCAGCAGTCT C 31

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTATGCATTT AAGCAGCAGC CGCGACTGG 29

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TCATTTAAAT GATGGAGTCT CTTCTCC 27

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCTTAATTAA TCAGCTCACA TGCGGG 26

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GTNGCNCCNW SNGAYATGAT GGA 23

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GCRTCNCKRA ANCCRTA 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTGGCTCCGA GTGATAT 17

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GCATCGCGAA AAGGACCG 18

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATCCATTGAA GCATCCAGGG TTATTGTCTC 30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GGATTGACGA AGCAGAGGAT GACGATGAGC 30

(2) INFORMATION FOR SEQ ID NO:15:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
AAATTGATGG CAAGATAGAC ATTGTATCCT GTACCTGTTC TTGGGCTGTG ACGGGGGGG       60
TGAAATTGAC GGTCATCACC CGGCTATTAT TACTATTGTT GTACTGTACA TCCGGATCCT    120
GCTGGTCTGT ATCTAGTTAG GGCAATATTC CCCGTCGCCA GGCCTCTTGG GTTATGAATG    180
ATTTCATAGG TGAAGTTTCG TATCCGTACG CACCGAGAGA TTTCTTAGTA TTACTTGTAT    240
TATGAAAATG CACTTGCCGA GTTAAGTCCG CCGGCCAATC ACGGCGGAGG ATATGGTAAG    300
CCGAAAAGTC TCGCCGAAGT CCCCGACTTA CTCTTACTGG AAGTGGCTTA GTGCCCTCAG    360
CGCCCCCTCG CCCTCAGTCC ATCAGCCAGA TTGACTCTTA TTTCTCTCTC CTCTTCGCCG    420
CGGGTGACAT ATCCCTCTCC TTCTCCCTCT CCCTCTTGAC AACATTTCAT CTTCGCTTCC    480
TTTTGTGATA TAGTCAGTTT CGCTATCCAT TGAAGCATCA CTCATGGAGT CTCTTCTCCA    540
GCAGTCCCGG GCGATGTGCC CGTTCCTTAA GCGCACATCT CCATCTTCTC TGCGTACGCT    600
GGCAACCGCG ACTCGACCTA GCACTAGTTC CGGTGGAGGC ACTATGTCTA ATCTCCAGGT    660
CATTGCCCGT CGCTGCCCTG TCATGAGCAA GGCTCTGGCC GTGCAGAGCC CAAATTGCAC    720
GGCAAGGAGG CGGCATTAGT CTTCAGCTCA TGCTTCGTGG CTAACGATGC CACCCTCGCA    780
ACCCTGGGTA GCAAGTTGCC CGACTGTGTT ATTCTGTCCG ATAGCCTGAA TCATGCATCG    840
ATGATTCAGG GTATTCGCCA TTCAGGCGCC AAGAAAATGG TTTTCAAGCA TAATGATCTG    900
GTCGACCTTG AGGCCAAGTT GGCAGCTCTA CCTCTTCATG TCCCCAAGAT TATTGCATTC    960
GAATCAGTTT ATAGCATGTG CGGATCTATT GCCCCAATTG AGAAGATCTG TGATCTTGCA   1020
GACAAGTACG GTGCCATTAC TTTCCTGGAT GAAGTCCACG CTGTGGGAAT GTACGGACCT   1080
CACGGAGCAG GTGTGGCAGA GCACCTTGAC TATGACATCT ATGCTTCCCA AGATACGGTC   1140
AACCCGCGCA GTACTAAGGG AACCGTGATG GACCGAATCG ATATTATCAC CGGTACTCTG   1200
GGCAAGGCCT ACGGATGTGT CGGGGGCTAC ATTGCTGGAT CCGCTGCGAT GGTTGACACC   1260
ATCCGCTCCC TCGCCCCTGG CTTCATCTTC ACCACGTCCT TGCCGCCCGC CACCATGGCT   1320
GGTGCAGACA CTGCTATCCA GTACCAGGCT CGTCACCAGG GCGACCGCGT CCTGCAGCAG   1380
TTGCACACCC GCGCGGTCAA AGCAGCTTTC AAGGAGTTGG ATATTCCTGT AATTCCCAAC   1440
CCCTCCCATA TCATTCCGCT CCTGGTTGGG GATGCCGAGG TTGCTAAGAA GGCCTCGGAC   1500
AAGCTTCTGG AGGAGCATGG AATTTATGTA CAAGCCATCA ACTACCCAAC CGTGCCTCGG   1560
GGTGAAGAGC GGCTTCGTAT CACGCCCACC CCGGGACATA TCAAGGAGCA CCGCGACCAC   1620
CTGGTGCAAG CCGTCCAAAC AGTCTGGAAC GAACTGGGCA TCAAACGCAC CAGCGATTGG   1680
GAAGCGCAAG GCGGCTTCGT CGGCGTGGGT GTCGATGGCG CCGAGGCTGA GAACCAGCCG   1740
ATTTGGAATG ATGTGCAGCT GGGGCTGAAG GAAAACGAAG CCATTGAGGC TGCTGTGGAA   1800
CGCGAGTTTG CCGAGGCCCC CATGCGGACC GCCACCCGTC CTGCCGCGGC TGCTGCTTCG   1860
TCAATCCCGG TGGGTGTGGC TGCCTGAAGT GGCTGCCCGC ATGTGAGCTG AAATCGACGT   1920
GGAATT                                                              1926
```

( 2 ) INFORMATION FOR SEQ ID NO:16:

( i ) SEQUENCE CHARACTERISTICS:
        ( A ) LENGTH: 449 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
Met  Glu  Ser  Leu  Leu  Gln  Gln  Ser  Arg  Ala  Met  Cys  Pro  Phe  Leu  Lys
 1                   5                        10                       15

Arg  Thr  Ser  Pro  Ser  Ser  Leu  Arg  Thr  Leu  Ala  Thr  Ala  Thr  Arg  Pro
              20                       25                       30

Ser  Thr  Ser  Ser  Gly  Gly  Gly  Thr  Met  Ser  Asn  Leu  Gln  Val  Ile  Ala
         35                        40                       45

Arg  Arg  Cys  Pro  Val  Met  Ser  Lys  Ala  Leu  Ala  Val  Gln  Ser  Pro  Asn
     50                        55                       60

Cys  Thr  Ala  Arg  Arg  Arg  His  Ser  Ser  Ala  His  Ala  Ser  Trp  Leu  Thr
65                       70                       75                        80

Met  Pro  Pro  Ser  Gln  Pro  Trp  Val  Ala  Ser  Cys  Pro  Thr  Val  Leu  Phe
                   85                        90                       95

Cys  Pro  Ile  Ala  Ile  Met  His  Arg  Phe  Arg  Val  Phe  Ala  Ile  Gln  Ala
              100                      105                      110

Pro  Arg  Lys  Trp  Phe  Ser  Ser  Ile  Met  Ile  Trp  Ser  Thr  Leu  Arg  Pro
         115                      120                      125

Ser  Trp  Gln  Leu  Tyr  Leu  Phe  Met  Ser  Pro  Arg  Leu  Leu  His  Ser  Asn
         130                      135                      140

Gln  Phe  Ile  Ala  Cys  Ala  Asp  Leu  Leu  Pro  Gln  Leu  Arg  Arg  Ser  Val
145                      150                      155                      160

Ile  Leu  Gln  Thr  Ser  Thr  Val  Pro  Leu  Leu  Ser  Trp  Met  Lys  Ser  Thr
              165                      170                      175

Leu  Trp  Glu  Cys  Thr  Asp  Leu  Thr  Glu  Gln  Val  Trp  Gln  Ser  Thr  Leu
              180                      185                      190

Thr  Met  Thr  Ser  Met  Leu  Pro  Lys  Ile  Arg  Ser  Thr  Arg  Ala  Val  Leu
         195                      200                      205

Arg  Glu  Pro  Trp  Thr  Glu  Ser  Ile  Leu  Ser  Pro  Val  Leu  Trp  Ala  Arg
     210                      215                      220

Pro  Thr  Asp  Val  Ser  Gly  Ala  Thr  Leu  Leu  Asp  Pro  Leu  Arg  Trp  Leu
225                      230                      235                      240

Thr  Pro  Ser  Ala  Pro  Ser  Pro  Leu  Ala  Ser  Ser  Ser  Pro  Arg  Pro  Cys
                   245                      250                      255

Arg  Pro  Pro  Pro  Trp  Leu  Val  Gln  Ala  Thr  Leu  Leu  Ser  Ser  Thr  Arg
              260                      265                      270

Leu  Val  Ala  Arg  Ala  Thr  Ala  Ser  Cys  Ser  Ser  Cys  Thr  Pro  Ala  Arg
         275                      280                      285

Ser  Lys  Gln  Leu  Ser  Arg  Ser  Trp  Ile  Phe  Leu  Phe  Pro  Thr  Pro  Pro
     290                      295                      300

Ile  Ser  Phe  Arg  Ser  Trp  Leu  Gly  Met  Pro  Arg  Leu  Leu  Arg  Arg  Pro
305                      310                      315                      320

Arg  Thr  Ser  Phe  Trp  Arg  Ser  Met  Glu  Phe  Met  Tyr  Lys  Pro  Ser  Thr
                   325                      330                      335

Thr  Gln  Pro  Cys  Leu  Gly  Val  Lys  Ser  Gly  Phe  Val  Ser  Arg  Pro  Pro
              340                      345                      350

Arg  Asp  Ile  Ser  Arg  Ser  Thr  Ala  Thr  Thr  Trp  Cys  Lys  Pro  Ser  Lys
              355                      360                      365

Gln  Ser  Gly  Thr  Asn  Trp  Ala  Ser  Asn  Ala  Pro  Ala  Ile  Gly  Lys  Arg
```

```
              370                    375                         380
Lys  Ala  Ala  Ser  Ser  Ala  Trp  Val  Ser  Met  Ala  Pro  Arg  Leu  Arg  Thr
385                      390                      395                      400

Ser  Arg  Phe  Gly  Met  Met  Cys  Ser  Trp  Gly  Arg  Lys  Thr  Lys  Pro  Leu
               405                           410                 415

Arg  Leu  Leu  Trp  Asn  Ala  Ser  Leu  Pro  Arg  Pro  Pro  Cys  Gly  Pro  Pro
               420                      425                      430

Pro  Val  Leu  Pro  Arg  Leu  Leu  Leu  Arg  Gln  Ser  Arg  Trp  Val  Trp  Leu
          435                      440                      445

Pro
```

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:17:

AATGGTCAAA ACTGGCTCCT AC        22

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

TGTACCTGTT CTTGGGCTGT C        21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

AGGCCTCTTG GGTTATGAAT G        21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TGACCTGGAG ATTAGACATA G        21

METHODS FOR PRODUCING POLYPEPTIDES IN RESPIRATORY-DEFICIENT CELLS

BACKGROUND OF THE INVENTION

1. Field of the Invention

The present invention relates to methods of producing polypeptides in respiratory-deficient mutant cells. The present invention also relates to methods for disrupting a gene in a respiratory-deficient mutant cell. The invention further relates to respiratory-deficient mutant cells and methods for obtaining such mutant cells.

2. Description of the Related Art

There are a variety of methods for selecting and maintaining a recombinant DNA molecule in a host cell. One method involves complementation of an auxotrophic mutation with a cloned wild-type gene. However, maintenance of complementing DNA in complex media is difficult where, for example, an amino acid or a nucleic acid may be present, which also relieves the auxotrophy. Another method employs marker genes that can be selected in wild-type recipients, particularly, resistance marker genes such as antibiotic resistance genes. The use of antibiotic resistance genes generally requires an expensive antibiotic in the culture medium and its subsequent removal from the desired product. A further method involves the use of a lethal chromosomal marker which is repressed by a gene borne by a recombinant DNA cloning vector. This method has been successfully applied to bacteria, but is difficult to apply to other hosts, e.g., fungi. Furthermore, the method requires the use of a plasmid-borne repressor gene that does not interfere with the transcriptional activating sequence driving expression of the recombinant DNA molecule.

The instability of an expression vector containing a recombinant DNA molecule in a host cell poses a serious problem for the consistent high-level expression of the recombinant DNA molecule. Upon subculturing of the transformant, the yield of a product encoded by the recombinant DNA molecule may decline dramatically and unpredictably. This is particularly true if expression of the recombinant DNA molecule imparts a deleterious effect on the host cell, e.g., toxicity of the expressed product toward the cell. It is desirable that a microbial culture of the transformant containing the recombinant DNA molecule be selected and maintained so that substantially all of the microbial cells in the culture will contain the recombinant DNA molecule.

There is a particular need in the art for alternative selection and maintenance systems that insure both high level expression and genetic stability of a transformant during cultivation.

U.S. Pat. No. 4,902,620 discloses the introduction of a heme biosynthetic enzyme (5-aminolevulinic acid synthase) gene into a heme-deficient cell for the production of 5-aminolevulinic acid.

It is an object of the present invention to provide new methods for selecting and maintaining recombinant cells in the heterologous expression of genes.

SUMMARY OF THE INVENTION

The present invention relates to methods of producing a polypeptide, comprising:

(a) introducing into a respiratory-defective mutant of a cell a nucleic acid construct comprising one or more first nucleic acid sequences and a second nucleic acid sequence, wherein the first nucleic acid sequence upon expression complements the respiratory defect and the second nucleic acid sequence encodes the polypeptide;

(b) cultivating the cell containing the first and second nucleic acid sequences in a culture medium under aerobic conditions suitable for expression of the first and second nucleic acid sequences; and (c) isolating the polypeptide from the cultivation medium of the cell.

The present invention also relates to methods for disrupting a gene in a respiratory-deficient mutant cell. The present invention further relates to respiratory-deficient mutant cells and methods for obtaining such mutant cells.

BRIEF DESCRIPTION OF THE FIGURES

FIG. 3 shows the nucleotide and deduced amino acid sequences of an *Aspergillus oryzae* IFO 4177 5-aminolevulinic acid synthase gene (SEQ ID NOS: 1 and 2, respectively).

FIG. 5 shows the nucleotide and deduced amino acid sequence of the *Aspergillus oryzae* IFO 4177 porphobilinogen synthase gene (SEQ ID NOS: 3 and 4, respectively).

FIG. 8 shows the nucleotide and deduced amino acid sequence of a hemA deletion allele (SEQ ID NOS: 15 and 16).

DETAILED DESCRIPTION OF THE INVENTION

Figure 1:
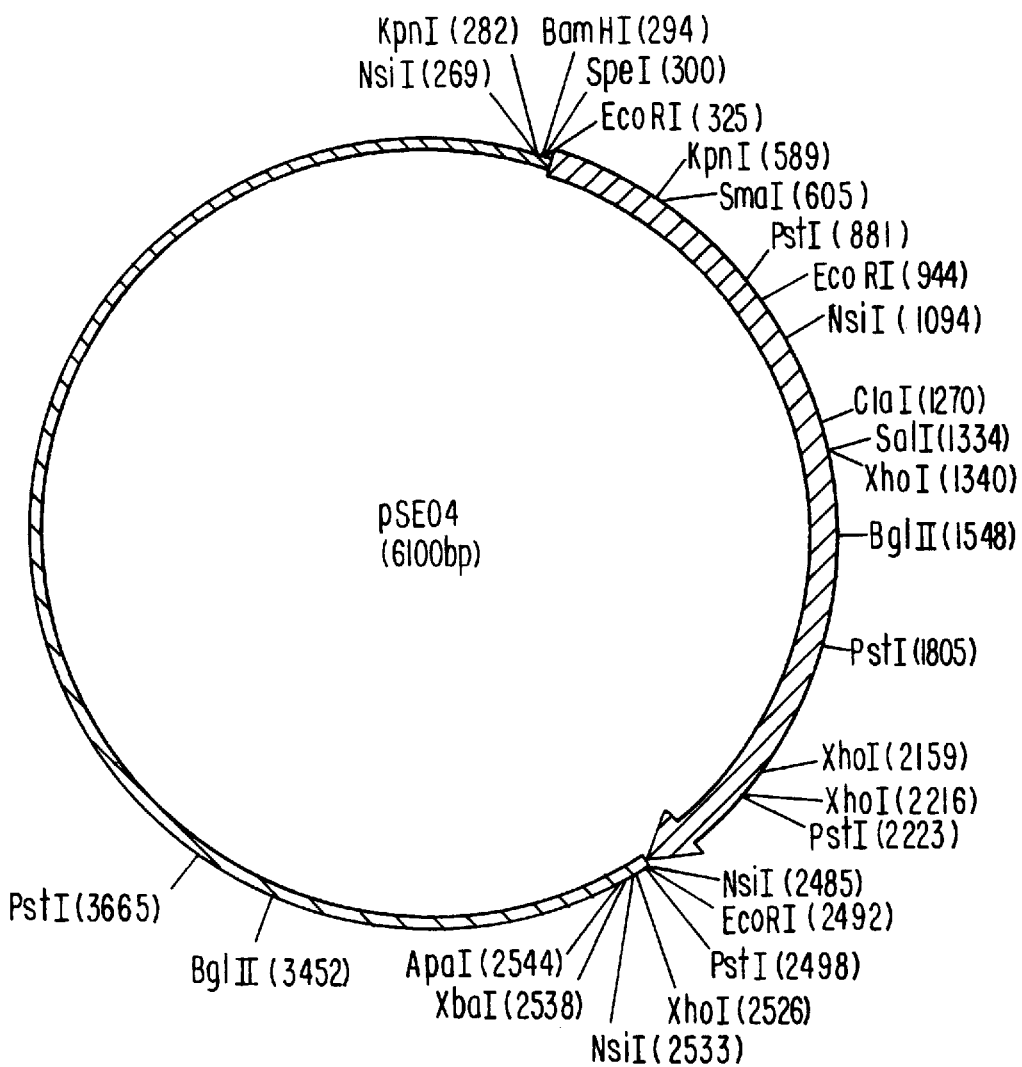
FIG. 1 shows a restriction map of plasmid pSE04.

The present invention relates to methods of producing a polypeptide, comprising:

(a) introducing into a respiratory-defective mutant of a cell a nucleic acid construct comprising one or more first nucleic acid sequences and a second nucleic acid sequence, wherein the first nucleic acid sequence upon expression complements the respiratory defect and the second nucleic acid sequence encodes the polypeptide;

(b) cultivating the cell containing the first and second nucleic acid sequences in a culture medium under aerobic conditions suitable for expression of the first and second nucleic acid sequences; and (c) isolating the polypeptide from the cultivation medium of the cell.

The methods of the present invention are based on the use of oxidative phosphorylation for selection of a cell in any relevant industrial fermentation medium where the only requirement is that the cell require oxygen for growth. The introduction of one or more first nucleic acid sequences into the respiratory-deficient mutant cell overcomes its respiratory deficiency and, therefore, can be selected based on the cell's ability to grow in the presence of oxygen. Thus, those mutant cells which contain the one or more first nucleic acid sequences can be cultivated in a culture medium, and therefore can be selected from mutant cells in which the introduction is not successful.

The term "oxidative phosphorylation" is a process which results in the formation of ATP as electrons are transferred from NADH to $FADH_2$ to $O_2$ by a series of electron carriers. NADH and $FADH_2$ are formed in glycolysis, fatty acid oxidation, and the citric acid cycle and are energy-rich molecules because each molecule has a pair of electrons with a high transfer potential. Oxidative phosphorylation is carried out by respiratory assemblies located, for example, in the inner mitochondrial membrane of eukaryotes or in the cell membrane of prokaryotes. The respiratory assemblies contain numerous electron carriers, such as the cytochromes. The step-by-step transfer of electrons from NADH or $FADH_2$ to $O_2$ through these carriers leads to the pumping of protons out of the mitochondrial matrix generating a proton-motive force. ATP is synthesized when protons flow back to the mitochondrial matrix through an enzyme complex. The ATP-generating process in which $O_2$ serves as the ultimate electron acceptor is called respiration. Organisms unable to transfer electrons through these carriers are respiratory-deficient.

The electrons are transferred from NADH to $O_2$ through a chain of three large proteins complexes called NADH-Q reductase (also called NADH dehydrogenase), cytochrome reductase, and cytochrome oxidase. The electron carrying groups in these enzymes are flavins, iron-sulfur clusters, hemes, and copper ions. Electrons are carried from NADH-Q reductase to cytochrome reductase by the reduced form of ubiquinone. Ubiquinone also carries electrons from $FADH_2$ to cytochrome reductase. Cytochrome c, a small protein, shuttles electrons from cytochrome reductase to cytochrome oxidase, the final component in the chain.

The first reaction is the oxidation of NADH by NADH-Q reductase, a flavoprotein that contains a tightly bound flavin mononucleotide (FMN) as its prosthetic group. Two electrons are transferred from NADH to FMN to produce the reduced form, $FMNH_2$. The electrons are then transferred from $FMNH_2$ to a series of iron-sulfur clusters, the second prosthetic group in NADH-Q reductase. The electrons in the iron-sulfur clusters of NADH-Q reductase are then shuttled to coenzyme Q (also known as ubiquinone). Ubiquinone is a quinone derivative with a long isoprenoid tail, which is reduced to ubiquinol by the uptake of a single electron. Ubiquinol is also the entry point for electrons from $FADH_2$.

Ubiquinol then transfers one of its two electrons to the iron-sulfur cluster in cytochrome reductase. A cytochrome is an electron-transporting protein that contains a heme prosthetic group. The function of cytochrome reductase is to catalyze the transfer of electrons from ubiquinol to cytochrome c. Cytochrome reductase contains cytochromes b and $c_1$ and an iron-sulfur cluster protein. The prosthetic group of cytochrome b, $c_1$, and c is iron-protoporphyrin IX, commonly known as heme. In cytochrome b, the heme is not covalently bonded to the protein, whereas in cytochromes c and $c_1$, the heme is covalently bonded to the protein by thioester linkages. Cytochromes a and $a_3$ have a different iron-porphyrin prosthetic group called heme A which differs from the heme in cytochromes c and $c_1$ in that a formyl group replaces one of the methyl groups, and a hydrocarbon chain replaces one of the vinyl groups. Ubiquinol transfers one of its two electrons to the iron-sulfur complex in the reductase which is then shuttled sequentially to cytochrome $c_1$ and c which carries it away from the complex. Cytochrome b enables ubiquinol to interact with the iron-sulfur cluster.

Cytochrome oxidase, which is comprised of cytochromes a and $a_3$, catalyzes the transfer of electrons from reduced cytochrome c to molecular oxygen, the final acceptor.

In the methods of the present invention, the respiratory-deficient mutant cell may be any cell which is defective in one or more genes resulting in one or more defective steps of the respiration process or has been rendered respiratory-deficient by disruption of one or more genes. These genes may include, but are not limited to, genes encoding any protein which is a component of the electron transport chain or genes encoding enzymes involved in the biosynthesis of flavin, the biosynthesis of quinone, or the biosynthesis of heme.

Respiratory-deficient mutants are oxidative-phosphorylation incompetent due to a lack of functional cytochromes. Disruption, therefore, totally eliminates growth in obligate aerobes. After disruption, the respiratory-deficient mutant is essentially an auxotroph that grows well only in media supplemented with a suitable substance to complement the deficiency and restore oxidative phosphorylation.

For example, the respiratory-deficient mutant cell may also be a cell wherein a regulatory gene which plays an important role in oxidative phosphorylation or a gene in a related pathway has been altered or disrupted, such as a gene which encodes an activator which mediates the activation of a heme biosynthetic gene. For example, induction of a *Saccharomyces cerevisiae* coproporphyrinogen oxidase gene occurs in part through the activation mediated by Cyp1p under heme-deficiency (Amillet et al., 1995, *Current Genetics* 28:503–511). Disruption of this gene could produce a cell which is heme-deficient and ultimately respiratory deficient.

Moreover, the mutant cell may be constructed by disrupting a gene important to oxidative phosphorylation using methods well known in the art such as insertion, deletion, or replacement of the nucleic acid residues in the gene. For example, one of the genes may be disrupted by inserting into the gene an integrative plasmid containing a nucleic acid fragment homologous to the gene which will create a duplication of the region of homology and incorporate vector DNA between the duplicated regions. This can eliminate gene expression if the inserted vector separates the promoter of the gene from the coding region or interrupts the coding sequence such that a non-functional gene product results. In addition, one or more of the control sequences which are necessary or advantageous for expression of one or more of the genes important to oxidative phosphorylation, e.g., promoter, may be modified. Alternatively, gene expression may be reduced or eliminated by the process of gene conversion (see, for example, Iglesias and Trautner, 1983, *Molecular General Genetics* 189: 73–76) or by gene replacement. In the latter process, a mutated version of the gene is introduced on a non-replicating linear fragment of DNA in association with a selectable marker. Selection for integration of the plasmid is effected by selection for the marker. Screening for the recombination event leading to gene replacement is effected by examination of colonies for acquisition of the mutated gene. Furthermore, reduction or elimination of expression of one or more genes important to oxidative phosphorylation may be accomplished by random mutagenesis using methods well known in the art, including, but not limited to, transposition and UV or chemical mutagenesis.

The choice of the respiratory-deficient mutant cell as a host cell will to a large extent depend upon several factors. One factor is the ability to complement the mutant cell's respiratory deficiency for growing the mutant cell prior to introducing the one or more first nucleic acid sequences. Complementation of the mutant cell's respiratory deficiency may be accomplished by supplementing the cultivation medium with a substance, e.g., a source of heme such as ferro-protoporphyrin or ferri-protoporphyrin (hemin) or with a hemoglobin to overcome disruption of a gene involved in the biosynthesis of heme. However, the choice will depend on the ability of the mutant cell to be rescued by the addition of the substance to a cultivation medium. Another important factor is whether the first nucleic acid sequence can be expressed in the host cell. A further factor is whether the second nucleic acid sequence can be expressed in the host cell.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell.

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein include the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed below. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast,* Bacil, M., Horecker, B. J., and Stopani, A. O. M., editors, 2nd edition, 1987; *The Yeasts,* Rose, A. H., and Harrison, J. S., editors, 2nd edition, 1987; and *The Molecular Biology of the Yeast Saccharomyces,* Strathern et al., editors, 1981).

In a more preferred embodiment, the yeast host cell is a cell of a species of Candida, Kluyveromyces, Saccharomyces, Schizosaccharomyces, Pichia, or Yarrowia.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillus foetidus, Aspergillus japonicus, Aspergillus niger* or *Aspergillus oryzae* cell. In another most preferred embodiment, the filamentous fungal host cell is a *Fusarium cerealis, Fusarium crookwellense, Fusarium graminearum, Fusarium oxysporum, Fusarium sambucinum, Fusarium sulphureum,* or *Fusarium venenatum* cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myce-* liophthora thermophilum cell. In another most preferred embodiment, the filamentous fungal host cell is a Neurospora crassa cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

In a preferred embodiment, one or more first nucleic acid sequences which encode one or more proteins which are components of the electron transport chain and results in the mutant being capable of complementing the respiratory defect, are introduced into the mutant. These proteins include NADH-Q reductase, cytochrome reductase (which comprises cytochrome b and $c_1$), cytochrome c, and cytochrome oxidase (which comprises cytochrome a and $a_3$).

In another preferred embodiment, one or more first nucleic acid sequences which encode one or more flavin biosynthetic enzymes which results in the mutant being capable of producing flavin, are introduced into the mutant.

In another preferred embodiment, one or more first nucleic acid sequences which encode one or more ubiquinone (or CoQ) biosynthetic enzymes which results in the mutant being capable of producing ubiquninone, are introduced into the mutant.

In another preferred embodiment, one or more first nucleic acid sequences which encode one or more heme biosynthetic enzymes which results in the mutant being capable of producing heme, are introduced into the mutant. Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme.

The term "heme biosynthetic enzyme" is defined herein to mean any enzyme involved in the biosynthesis of heme. Examples of such heme biosynthetic enzymes include, but are not limited to, 5-aminolevulinic acid synthase (EC 2.3.1.37), porphobilinogen synthase (EC 4.2.1.24), porphobilinogen deaminase (EC 4.3.1.8), uroporphyrinogen III synthase (EC 4.2.11.75), uroporphyrinogen III decarboxylase (EC 4.1.1.37), coproporphyrinogen III oxidase (EC 1.3.3.3), protoporphyrinogen IX oxidase (EC 1.3.3.4), and ferrochelatase (EC 4.99.1.1). 5-Aminolevulinic acid synthase catalyzes the condensation of glycine and succinyl-CoA to form 5-aminolevulinic acid. Porphobilinogen synthase (also called 5-aminolevulinic acid dehydratase or 5-aminolevulinic acid dehydrase) catalyzes the condensation of two molecules of 5-aminolevulinic acid to form porphobilinogen. Porphobilinogen deaminase (also called hydroxymethylbilane synthase or uro I synthase) catalyzes the tetrapolymerization of pyrole porphobilinogen into preuroporphyrinogen. Uroporphyrinogen III synthase (also called uro III synthase or uro III cosynthase) catalyzes a rearrangement of the fourth ring of preuroporphyrinogen followed by cyclization to produce uroporphyrinogen III. Uroporphyrinogen III decarboxylase (also called uro D or uroporphyrinogen decarboxylase) catalyzes the decarboxylation of all four acetic acid side chains of uroporphyrinogen III to methyl groups to yield coproporphyrinogen III. Coproporphyrinogen III oxidase (also called coproporphyrinogenase) catalyzes the oxidative decarboxylation of two propionate groups at positions 2 and 4 on the A and B rings of coproporphyrinogen III to vinyl groups yielding protoporphyrinogen IX. Protoporphyrinogen IX oxidase catalyzes a six electron oxidation of protoporphyrinogen IX to yield protoporphyrin IX. Ferrochelatase (also called ferrolyase, heme synthase, or protoheme ferrolyase) catalyzes the insertion of iron into the protoporphyrin to yield heme.

The biosynthesis of 5-aminolevulinic acid may occur alternatively from glutamate by means of a tRNA-Glu mediated pathway. The glutamate pathway is found in many anaerobic bacteria, plants, and organisms capable of photosynthesis. The biosynthesis of 5-aminolevulinic acid from glutamate involves three enzymatic steps catalyzed by glutamate tRNA$_{glu}$ synthase (EC 6.1.1.17), glutamate tRNA$_{glu}$ reductase, and glutamate 1-semialdehyde aminotransferase. Glutamate tRNA$_{glu}$ synthetase (also called glutamate-tRNA$_{glu}$ synthase) catalyzes the the coupling of glutamate to tRNA in the presence of ATP and magnesium ions. Glutamate tRNA$_{glu}$ reductase (also called glutamate-tRNA$_{glu}$ dehydrogenase) catalyzes the reduction of tRNA bound glutamate in the presence of NADPH to glutamate 1-semialdehyde. Glutamate 1-semialdehyde aminotransferase (also called glutamate 1-semialdehyde aminomutase) catalyzes the conversion of glutamate 1-semialdehyde to 5-aminonlevulinic acid.

The first nucleic acid sequence is preferably a sequence encoding a heme biosynthetic enzyme selected from the group consisting of a 5-aminolevulinic acid synthase, a porphobilinogen synthase, a porphobilinogen deaminase, an uroporphyrinogen synthase, an uroporphyrinogen decarboxylase, a coproporphyrinogen oxidase, a protoporphyrinogen oxidase, a ferrochelatase, and a glutamate-tRNA$_{glu}$ synthase, a glutamate-tRNA$_{glu}$ reductase, a glutamate 1-semialdehyde aminotransferase. The first nucleic acid sequence may be obtained from any microbial source and may be native or foreign to the host cell. The choice of the source of the first nucleic acid sequence will depend on the heme-deficient mutant cell to be used as a host cell, but preferred sources are fungal sources, e.g., yeast and filamentous fungi. Preferred filamentous fungal sources include, but are not limited to, species of Acremonium, Aspergillus, Fusarium, Humicola, Myceliophthora, Mucor, Neurospora, Penicillium, Phanerochaete, Thielavia, Tolypocladium, and Trichoderma. Preferred yeast sources include, but are not limited to, species of Candida, Kluyveromyces, Pichia, Saccharomyces, Schizosaccharomyces, and Yarrowia.

The first nucleic sequence encoding a heme biosynthetic enzyme may be one of the following:

1. 5-Aminolevulinic acid synthase genes:
    a. *Saccharomyces cerevisiae* (Urban-Grimal et al., 1986, *European Journal of Biochemistry* 156: 511–59);
    b. *Aspergillus nidulans* (Bradshaw et al., 1993, *Current Genetics* 23: 501–507);
    c. *Rhodobacter sphaeroides* (Tai et al., 1988, *Gene* 70: 139–152);
    d. *Rhodobacter capsulatus* (Hornberger et al., 1990, *Molecular General Genetics* 211: 371–378); and
    e. *Escherichia coli* (Drolet et al., 1989, *Molecular General Genetics* 216: 347–352).
2. Porphobilinogen synthase genes:
    a. *Saccharomyces cerevisiae* (Myers et al., 1987, *Journal of Biological Chemistry* 262: 16822–16829);
    b. *Staphylococcus aureus* (Kafala and Sasarman, 1994, *Canadian Journal of Microbiology* 40: 651–657);
    c. *Rhodobacter sphaeroides* (Delaunay et al., 1991, *Journal of Bacteriology* 173: 2712–2715);
    d. *Escherichia coli* (Echelard et al., 1988, *Molecular General Genetics* 214: 503–508); and e. *Bacillus subtilis* (Hansson et al., 1991, *Journal of Bacteriology* 173: 2590–2599).
3. Porphobilinogen deaminase genes
   a. *Saccharomyces cerevisiae* (Keng et al., 1992, *Molecular General Genetics* 234: 33–43);
   b. human (Yoo et al., 1993, *Genomics* 15:221–29; Raich et al., 1986, *Nucleic Acids Research* 14: 5955–5968);
   c. *Escherichia coli* (Thomas and Jordan, 1986, *Nucleic Acids Research* 14: 6215–6226); and
   d. *Bacillus subtilis* (Petricek et al., 1990, *Journal of Bacteriology* 172: 2250–2258).
4. Uroporphyrinogen III synthase genes:
   a. *Saccharomyces cerevisiae* (Amillet and Labbe-Bois, 1995, *Yeast* 11: 419–424);
   b. *Bacillus subtilis* (Hansson et al., 1991, *Journal of Bacteriology* 173: 2590–2599); and
   c. *Escherichia coli* (Jordan et al., 1987, *Nucleic Acids Research*. 15: 10583).
5. Uroporphyrinogen III decarboxylase genes:
   a. *Saccharomyces cerevisiae* (Garey et al., 1992, *European Journal of Biochemistry* 205: 1011–1016); and
   b. human (Romeo et al., 1986, *Journal of Biological Chemistry* 261: 9825–9831).
6. Coproporphyrinogen III oxidase genes:
   a. human (Martasek et al., 1994, *Proceedings of the National Academy of Sciences USA* 911: 3024–3028);
   b. *Escherichia coli* (Troup et al., 1994, *Journal of Bacteriology* 176: 673–680); and
   c. *Saccharomyces cerevisiae* (Zaagorec et al., 1986, *Journal of Biological Chemistry* 263: 9718–9724).
7. Protoporphyrinogen IX oxidase genes:
   a. human (Taketani et al., 1995, *Genomics* 29: 698–703);
   b. *Bacillus subtilis* (Dailey et al., 1994, *Journal of Biological Chemistry* 269: 813–815); and
   c. *Escherichia coli* (Sasarman et al., 1993, *Canadian Journal of Microbiology* 39: 155–161).
8. Ferrochelatase genes:
   a. *Saccharomyces cerevisiae* (Labbe-Bois, 1990, *Journal of Biological Chemistry* 265: 7278–7283);
   b. bovine (Shibuya et al., 1995, *Biochimica Biophysica Acta* 1231: 117–120);
   c. *Bradyrhizobium japonicum* (Frustaci and O'Brian, 1993, *Applied Environmental Microbiology* 59: 2347–2351);
   d. *Escherichia coli* (Frustaci and O'Brian, 1993, *Journal of Bacteriology* 175: 2154–2156); and
   e. *Bacillus subtilis* (Hansson and Hederstedt, 1992, *Journal of Bacteriology* 174: 8081–8093).
9. Glutamate-tRNA$_{glu}$ synthetase genes
   a. *Methanobacterium thermoautotrophicum* (Moore et al., 1996, *Biochimica et Biophysica Acta* 1305: 113–116.
   b. *Thermus thermophilus* (Nureki et al., 1992, *European Journal of Biochemistry* 204: 465–472).
   c. *Bacillus subtilis* (Breton et al., 1990, *Journal of Biological Chemistry* 265: 18248–18255).
   d. *Bacillus stearothermophilus* (Breton et al., 1990, *Journal of Biological Chemistry* 265: 18248–18255).
   e. *Saccharomyces cerevisiae* (Ludmerer and Schimmel, 1985, *Journal of Bacteriology* 163: 763–768).
   f. *E. coli* (Breton et al., 1986, *Journal of Biological Chemistry* 261: 10610–10617).
10. Glutamate-tRNA$_{glu}$ reductase genes
    a. Barley (Vothknecht et al., 1996, *Proceedings of the National Academy of Sciences USA* 93: 9287–9291).
    b. *Pseudomonas aeruginosa* (Hungerer et al., 1995, *Molecular and General Genetics* 248: 375–380).
    c. *E. coli* (Ikemi et al., 1992, *Gene* 121: 127–132).
    d. *Bacillus subtilis* (Petricek et al., 1990, *Journal of Bacteriology* 172: 2250–2258).
    e. *Methanobacterium thermoautotrophicum* (Hungerer et al., 1996, *Bioorg. Med. Chem.* 4: 1089–1095).
11. Glutamate 1-semialdehyde aminotransferase genes
    a. *Salmonella typhimurium* (Elliott et al., 1990, *Journal of Bacteriology* 172: 7071–7084).
    b. Barley (Grimm, 1990, *Proceedings of the National Academy of Sciences USA* 87: 4169–4173).
    c. *E. coli* (Ikemi et al., 1992, *Gene* 121: 127–132).

In a more preferred embodiment, the first nucleic acid sequence is obtained from a species of Aspergillus. In an even more preferred embodiment, the first nucleic acid sequence is obtained from *Aspergillus ficuum, Aspergillus foetidus, Aspergillus japonicus, Aspergillus niger, Aspergillus nidulans,* or *Aspergillus oryzae*. In another more preferred embodiment, the first nucleic acid sequence is obtained from a species of Saccharomyces. In an even more preferred embodiment, the first nucleic acid sequence is obtained from *Saccharomyces cerevisiae, Saccharomyces carlsbergensis, Saccharomyces diastaticus, Saccharomyces douglasii, Saccharomyces kluyveri, Saccharomyces norbensis,* or *Saccharomyces oviformis*.

In a most preferred embodiment, the first nucleic acid sequence encoding a 5-aminolevulinic acid synthase is obtained from *Aspergillus oryzae* strain A1560 (IFO 4177), e.g., the nucleic acid sequence set forth in SEQ ID NO:1. The first nucleic sequence may also be a nucleic acid sequence coding for the 5-aminolevulinic acid synthase having the amino acid sequence set forth in SEQ ID NO:2, which differs from SEQ ID NO:1 by virtue of the degeneracy of the genetic code. In another most preferred embodiment, the first nucleic acid sequence encoding a porphobilinogen synthase is obtained from *Aspergillus oryzae* strain A1560 (IFO 4177), e.g., the nucleic acid sequence set forth in SEQ ID NO:3. The first nucleic acid may further be a nucleic acid sequence coding for the porphobilinogen synthase having the amino acid sequence set forth in SEQ ID NO:4, which differs from SEQ ID NO:3 by virtue of the degeneracy of the genetic code. The first nucleic acid sequences of the present invention further encompass both the genomic sequences depicted in SEQ ID NO:1 and SEQ ID NO:3 as well as the corresponding cDNA and RNA sequences. The phrase "nucleic acid sequences" as used herein will be understood to encompass all such variations including synthetic DNA.

In an effort to maximize plasmid copy number, expression of the first nucleic acid sequence may be crippled, for example, by truncating/mutating a promoter to reduce the level of transcription requiring multiple copies of the vector to be integrated to support rapid growth in the absence of a heme or a heme precursor. Any mutation which reduces transcription of the introduced first nucleic acid sequence may be used. Furthermore, mutations in the amino acid sequence of a protein expressed by the first nucleic acid sequence which result in a reduction in activity of the protein may be used to maximize the copy number. For example, any mutation which reduces enzymatic activity of a introduced heme biosynthetic gene may be used.

The second nucleic acid sequence encoding the polypeptide may be native or heterologous to the mutant cell. In the case of a heterologous polypeptide, the nucleic acid sequence encoding the heterologous polypeptide may be obtained from any prokaryotic, eukaryotic, or other source, e.g., archaeabacteria. The term "polypeptide" is not meant herein to refer to a specific length of the encoded product and, therefore, encompasses peptides, oligopeptides, and proteins. The term ÒpolypeptideÓ also encompasses two or more polypeptides combined to form the encoded product. Polypeptides also include hybrid polypeptides which comprise a combination of partial or complete polypeptide sequences obtained from at least two different polypeptides wherein one or more may be heterologous to the host cell. Polypeptides further include naturally occurring allelic and engineered variations of the above mentioned polypeptides.

The polypeptide may be an enzyme, a hormone, a hormone variant, a receptor or a portion thereof, an antibody or a portion thereof, or a reporter. In a more preferred embodiment, the polypeptide is an oxidoreductase, a transferase, a hydrolase, a lyase, an isomerase, or a ligase. In an even more preferred embodiment, the polypeptide is an aminopeptidase, an amylase, a carbohydrase, a carboxypeptidase, a catalase, a cellulase, a chitinase, a cyclodextrin glycosyltransferase, a cutinase, a deoxyribonuclease, an esterase, an alpha-galactosidase, a beta-galactosidase, a glucoamylase, an alpha-glucosidase, a beta-glucosidase, a glutaminase, a haloperoxidase, an invertase, a laccase, a lipase, a mannosidase, a mutanase, an oxidase, a pectinolytic enzyme, a peroxidase, a phytase, a polyphenoloxidase, a proteolytic enzyme, a ribonuclease, a transglutaminase, or a xylanase.

The methods of the present invention also encompass, within the scope of the term "native polypeptide", such recombinant production of polypeptides native or endogenous to the mutant cell, to the extent that such expression involves the use of genetic elements not native to the host cell, or use of native elements which have been manipulated to function in a manner not normally found in the host cell. For example, native polypeptides may be recombinantly produced by, e.g., placing a gene encoding the polypeptide under the control of a different promoter to enhance expression of the polypeptide or under control of a different signal sequence to expedite export of a native polypeptide outside the cell, and increasing the copy number of a gene encoding the polypeptide normally produced by the host cell.

The polypeptide may also be a hemoprotein. "Hemoprotein" is defined herein as any member of a group of proteins containing heme as a prosthetic group. The hemoprotein may be a globin, a cytochrome, an oxidoreductase, or any other protein containing a heme as a prosthetic group. Heme-containing globins include hemoglobin and myoglobin. Heme-containing cytochromes include cytochrome P450, cytochrome b, cytochrome $c_1$, and cytochrome c. Heme-containing oxidoreductases include, but are not limited to, a catalase, an oxidase, an oxygenase, a haloperoxidase, and a peroxidase. In a preferred embodiment, the oxidoreductase is a catalase. In another preferred embodiment, the oxidoreductase is an oxidase. In another preferred embodiment, the oxidoreductase is an oxygenase. In another preferred embodiment, the oxidoreductase is a haloperoxidase. In another preferred embodiment, the oxidoreductase is a peroxidase. In a more preferred embodiment, the peroxidase is obtained from a Coprinus strain, an Arthromyces strain, or a Phanerochaete strain. In an even more preferred embodiment, the peroxidase is obtained from a *Coprinus cinereus* strain, e.g., *Coprinus cinereus* IFO 8371, a *Coprinus macrorhizus* strain, or an *Arthromyces ramosus* strain. In another more preferred embodiment, the catalase is obtained from a Scytalidium strain, an Aspergillus strain, or a Humicola strain. In another even more preferred embodiment, the catalase is obtained from a *Scytalidium thermophilum* strain, e.g., *Scytalidium thermophilum* CBS 117.65, an Aspergillus niger strain, or a *Humicola insolens* strain.

The first and second nucleic acid sequences are preferably contained in a nucleic acid construct. The term "nucleic acid construct" is defined herein to mean a nucleic acid molecule, either single- or double-stranded, which is isolated from a naturally occurring gene or which has been modified to contain segments of nucleic acids which are combined and juxtaposed in a manner which would not otherwise exist in nature. The term nucleic acid construct may be synonymous with the term expression cassette when the nucleic acid construct contains all the control sequences required for expression of a coding sequence. The term "coding sequence" as defined herein is a sequence which is transcribed into mRNA and translated into a polypeptide when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

The first nucleic acid sequence may be manipulated in a variety of ways to provide for expression of the enzyme or to reduce expression in order to boost the copy number of the first nucleic acid sequence. Manipulation of the nucleic acid sequence prior to its insertion into a vector may be desirable or necessary depending on the expression vector. The techniques for modifying nucleic acid sequences utilizing, for example, cloning methods and mutagenesis are well known in the art.

The term "control sequences" is meant herein to include all components which are necessary or advantageous for expression of the coding sequence of the first nucleic acid sequence. The control sequences may be native to the first nucleic acid sequence, may be obtained from other sources, or may be a combination of native and foreign control sequences. The foreign control sequences may simply replace or be added to the natural control sequences in order to obtain enhanced expression of the first nucleic acid sequence relative to the natural control sequence normally associated with the coding sequence. Such control sequences include, but are not limited to, a leader, a polyadenylation sequence, a propeptide sequence, a promoter, a signal sequence, and a transcription terminator. For expression under the direction of control sequences, the first nucleic acid sequence to be used according to the present invention is operably linked to the control sequences in such a way that expression of the coding sequence of the first nucleic acid sequence is achieved under conditions compatible with the control sequences. The term "coding sequence" as defined herein is a sequence which is transcribed into mRNA and translated into a product when placed under the control of the above mentioned control sequences. The boundaries of the coding sequence are determined by a translation start codon at the 5'-terminus and a translation stop codon at the 3'-terminus. A coding sequence can include, but is not limited to, DNA, cDNA, and recombinant nucleic acid sequences.

The first control sequence may be an appropriate promoter sequence, a nucleic acid sequence which is recognized by the host cell for expression of the first nucleic acid sequence. The promoter sequence contains transcriptional control sequences which mediate the expression of the heme biosynthetic enzyme. The promoter may be any promoter sequence which shows transcriptional activity in the host cell of choice including a mutant, truncated, or hybrid promoter. The promoter may be obtained from genes either homologous or heterologous to the host cell.

Examples of suitable promoters for directing the transcription of the first nucleic acid sequence, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothemophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727–3731), as well as the tac promoter (DeBoer et al., 1983, *Proceedings of the National Academy of Sciences USA* 80:21–25). Further promoters are described in "Useful proteins from recombinant bacteria" in *Scientific American*, 1980, 242:74–94; and in Sambrook et al., *Molecular Cloning, A Laboratory Manual*, 2d ed., Cold Spring Harbor, New York, 1989).

Examples of suitable promoters for directing the transcription of the first nucleic acid sequence in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and mutant, truncated, and hybrid promoters thereof. Particularly preferred promoters for use in filamentous fungal host cells are the TAKA amylase, NA2-tpi (a hybrid of the promoters from the genes encoding *Aspergillus niger* neutral a-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8:423–488. In a mammalian host cell, useful promoters include viral promoters such as those from Simian Virus 40 (SV40), Rous sarcoma virus (RSV), adenovirus, and bovine papilloma virus (BPV).

The first control sequence may also be a suitable transcription terminator sequence, a sequence recognized by the host cell to terminate transcription. The terminator sequence is operably linked to the 3' terminus of the first nucleic acid sequence. The terminator sequence may be native to the first nucleic acid sequence or may be obtained from other sources, i.e., a foreign terminator sequence. Any terminator which is functional in the host cell of choice is likely to be useful in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The first control sequence may also be a suitable leader sequence, a nontranslated region of a mRNA which is important for translation by the host cell. The leader sequence is operably linked to the 5' terminus of the first nucleic acid sequence. The leader sequence may be native to the first nucleic acid sequence or may be obtained from other sources, i.e., a foreign leader sequence. Any leader sequence which is functional in the host cell of choice is likely to be useful in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The first control sequence may also be a polyadenylation sequence, a sequence which is operably linked to the 3' terminus of the first nucleic acid sequence and which, when transcribed, is recognized by the host cell to add polyadenosine residues to transcribed mRNA. The polyadenylation sequence may be native to the first nucleic acid sequence or may be obtained from other sources, i.e., a foreign polyadenylation sequence. Any polyadenylation sequence which is functional in the host cell of choice is likely to be useful in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15:5983–5990. Polyadenylation sequences are well known in the art for mammalian host cells.

The first control sequence may also be a signal peptide coding region, which codes for an amino acid sequence linked to the amino terminus of the expressed protein, permitting the localization of the protein to a particular cellular compartment. The signal peptide coding region may be native to the first nucleic acid sequence or may be obtained from foreign sources. The 5' end of the coding sequence of the first nucleic acid sequence may inherently contain a signal peptide coding region naturally linked in translation reading frame with the segment of the coding region which encodes the localized protein. Alternatively, the 5' end of the coding sequence may contain nucleic acids encoding a signal peptide coding region which is foreign to that portion of the coding sequence which encodes the localized protein. Any signal peptide coding region capable of permitting localization of the protein in a host cell of choice may be used in the present invention.

The first control sequence may also be a propeptide coding region which codes for an amino acid sequence positioned at the amino terminus of a mature biochemically active polypeptide. The resultant polypeptide is known as a proenzyme or a propolypeptide (or a zymogen in some cases). Proenzymes are generally inactive and can be converted to mature active polypeptides by catalytic or autocatalytic cleavage of the propeptide from the proenzyme. A biochemically active polypeptide is defined herein as a polypeptide which is produced in active form which performs the biochemical activity of its natural counterpart. The propeptide sequence may be native to the first nucleic acid sequence encoding the heme biosynthetic enzyme or may be obtained from other sources, i.e., a foreign propeptide sequence. The nucleic acid sequence encoding a propeptide may be obtained from the genes encoding the *Bacillus subtilis* alkaline protease (aprE), *Bacillus subtilis* neutral protease gene (nprT), *Saccharomyces cerevisiae* alpha-factor, and *Myceliophthora thermophilum* laccase.

In a preferred embodiment, the second nucleic acid sequence is introduced into the host cell, operably linked to one or more second control sequences. The second control sequences may be native to the second nucleic acid sequences encoding the polypeptide or may be partially or wholly obtained from foreign sources. The foreign control sequences may simply replace the natural control sequences in order to obtain enhanced production of the desired polypeptide relative to the natural control sequence normally associated with the coding sequence. The second control sequences can be any of the control sequences exemplified above in connection with the first control sequences.

In the case of signal peptide coding regions which can direct the expressed polypeptide into the cell's secretory pathway, there are several possibilities. An effective signal peptide coding region for bacterial host cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, *Microbiological Reviews* 57:109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The first and second nucleic acid sequences can be introduced into the mutant host cell using methods well known in the art. For example, the sequences may be introduced and integrated into the host genome by homologous or non-homologous recombination where one or more copies of the sequences are integrated into a single target sequence and/or multiple target sequences. Alternatively, the sequences may be introduced and maintained as a non-integrated expression vector, e.g., a self-replicating extrachromosomal plasmid.

The first and second nucleic acid sequences are preferably contained in the same nucleic acid construct to force selection of both nucleic acid sequences together, but they may be contained in different nucleic acid constructs. Each nucleic acid construct may comprise integrational elements for directing integration by homologous recombination into the genome of the host cell at a precise location. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, each nucleic acid construct may be integrated into the genome of the host cell by non-homologous recombination.

The nucleic acid constructs may be inserted into a suitable vector or the coding regions of the first and second nucleic acid sequences may be inserted directly into a vector which already contains the control sequences. The first and second nucleic acid sequences or constructs may also be contained on separate vectors. The vectors may be any vector which can be conveniently subjected to recombinant DNA procedures and can bring about the expression of a nucleic acid sequence of the present invention. The choice of a vector will typically depend on the compatibility of the vector with the host cell into which the vector is to be introduced. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. Alternatively, the vector may be one which, when introduced into the cell, is integrated into the genome and replicated together with the chromosome(s) into which it has been integrated. The vector system may be a single vector or two or more vectors which together contain the total DNA to be introduced into the genome of the host cell.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in Bacillus. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

The procedures used to ligate the nucleic acid constructs, the promoter, terminator and other elements, and to insert them into suitable vectors containing the information necessary for replication, are well known to persons of ordinary skill in the art (cf., for instance, Sambrook et al., 1989, supra).

The transformation of a bacterial host cell may, for instance, be effected by protoplast transformation (see, e.g., Chang and Cohen, 1979, *Molecular General Genetics* 168:111–115), by using competent cells (see, e.g., Young and Spizizin, 1961, *Journal of Bacteriology* 81:823–829, or Dubnau and Davidoff-Abelson, 1971, *Journal of Molecular Biology* 56:209–221), by electroporation (see, e.g., Shigekawa and Dower, 1988, *Biotechniques* 6:742–751), or by conjugation (see, e.g., Koehler and Thorne, 1987, *Journal of Bacteriology* 169:5771–5278).

A standard procedure in the art for introducing a nucleic acid sequence into a filamentous fungal cell involves protoplast formation, transformation of the protoplasts, and regeneration of the cell wall of the transformed protoplasts in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78:147–156 or in copending U.S. Ser. No. 08/269,449, now abandoned.

Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920.

Mammalian cells may be transformed by direct uptake using the calcium phosphate precipitation method of Graham and Van der Eb (1978, *Virology* 52:546).

In the methods of the present invention, the cells are cultivated in a nutrient medium suitable for production of the polypeptide and the heme biosynthetic enzymes using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, for example, Bennett, J. W. and LaSure, L., eds., *More Gene Manipulations in Fungi*, Academic Press, Calif., 1991). Suitable media are available from commercial suppliers or may be prepared using published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of a polypeptide if it possesses enzyme activity.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The present invention also relates to methods for disrupting a gene in a heme-deficient mutant cell. The methods comprise:

(a) replacing the gene in the heme-deficient mutant cell by introducing a nucleic acid construct comprising a third nucleic acid sequence containing the gene or a portion thereof and a first nucleic acid sequence within the gene or portion therof, wherein the first nucleic acid sequence encodes a heme biosynthetic enzyme and the introduction of the first nucleic acid sequence results in the mutant being capable of producing heme; and (b) cultivating the cell containing the first and third nucleic acid sequences in a heme-free and heme intermediate-free culture medium under conditions suitable for expression of the first nucleic acid sequence.

Disruption of a gene endogenous to a cell may be accomplished using methods well known in the art such as insertion, deletion, or replacement of the nucleic acid residues in the gene such as those methods described above. The third nucleic acid sequence may be any sequence (which is desired to create a defect or marked allele) which upon integration into the targeted gene disrupts the gene to reduce or eliminate expression. The third sequence may be a subsequence of any of the second nucleic acid sequences mentioned above. In order to insure integration into the endogenous gene, the construct should contain integrational elements as described earlier.

The present invention also relates to respiratory-deficient mutants of a cell comprising a first nucleic acid sequence which comprises a modification of at least one of the genes essential to oxidative phosphorylation, wherein the mutant is respiratory-deficient compared to the cell when cultured under the same conditions. In a preferred embodiment, the respiratory-deficient mutant is heme-deficient.

The present invention also relates to methods of obtaining a respiratory-deficient mutant of a cell, comprising (a) introducing into the cell a nucleic acid sequence comprising a modification of at least one of the genes essential to oxidative phosphorylation; and (b) identifying a mutant of the cell from step (a) comprising the nucleic acid sequence, wherein the mutant is respiratory-deficient when cultured under the same conditions as the cell. In a preferred embodiment, the mutant is heme-deficient.

The present invention is further described by the following examples which should not be construed as limiting the scope of the invention.

EXAMPLES

Example 1

*Aspergillus oryzae* strain A1560 genomic DNA extraction

*Aspergillus oryzae* strain A1560 (IFO 4177) was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3M solution) was added to a final concentration of 0.3M followed by addition of 2.5 volumes of ice cold ethanol to precipitate the nucleic acids. The nucleic acids were then pelleted by centrifuging the tube at 15,000×g for 30 minutes. The pellet was allowed to air dry for 30 minutes before resuspension in 0.5 ml of TE buffer. DNase-free ribonuclease A was added to a concentration of 100 μg/ml and the mixture was incubated at 37° C. for 30 minutes. Proteinase K was then added at a concentration of 200 μg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 2
Construction of plasmid pSE04

Genomic DNA was obtained from *Aspergillus nidulans* strain A26 (Fungal Genetics Stock Center, Kansas City, Kans.) using the same procedure described in Example 1. Plasmid pSE04 was constructed by ligation of PCR fragments from an amplification reaction containing *Aspergillus nidulans* A26 genomic DNA. The amplification reaction contains the following components: 50 ng of *Aspergillus nidulans* A26 genomic DNA, 100 μM each of dATP, dCTP, dGTP, and dTTP (Boehringer Mannheim, Indianapolis, Ind.), 50 pmoles of primers ALAS3d 5' TTTATGATGGAG-GCCCTTCTCCAGCAGTCTC 3' (SEQ ID NO:5) and ALAS4e 5' CTATGCATTTAAGCAGCAGCCGC-GACTGG 3' (SEQ ID NO:6), 2 units of Taq DNA polymerase (Perkin-Elmer Corp., Branchburg, N.J.), and IX Taq DNA polymerase buffer (Perkin-Elmer Corp., Branchburg, N.J.). The reaction was incubated in a Perkin-Elmer Thermal Cycler (Perkin-Elmer Corp., Branchburg, N.J.) programmed for 30 cycles each at 95° C. for 1 minute, 55° C. for 1 minute, and 72° C. for 90 seconds. The 2 kb PCR product was isolated by excision after electrophoresis using a 1.1% low melting temperature agarose gel (FMC, Rockland, Me.) with 40 mM Tris-acetate-1 mM disodium EDTA (TAE) buffer, and subcloned into the pCRII vector (Invitrogen, San Diego, Calif.) according to the manufacturer's instructions to produce pSE04 (FIG. 1).

Example 3
*Aspergillus oryzae* strain A1560 DNA libraries and identification of ALA synthase (hemA) clones

*Aspergillus oryzae* strain A1560 genomic DNA libraries were constructed using the bacteriophage cloning vector λZipLox (Life Technologies, Gaithersburg, Md.) according to the manufacturer's instructions using *E. coli* Y1090ZL cells as a host for plating and purification of recombinant bacteriophage and *E. coli* DH10Bzip for excision of individual pZL1-hemA clones. Total cellular DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 4–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms, and the ligation mixtures were packaged using commercial packaging extracts (Stratagene, La Jolla, Calif.). The packaged DNA libraries were plated and amplified in *E. coli* Y1090ZL cells. The unamplified genomic library contains $1 \times 10^6$ pfu/ml.

Figure 2:
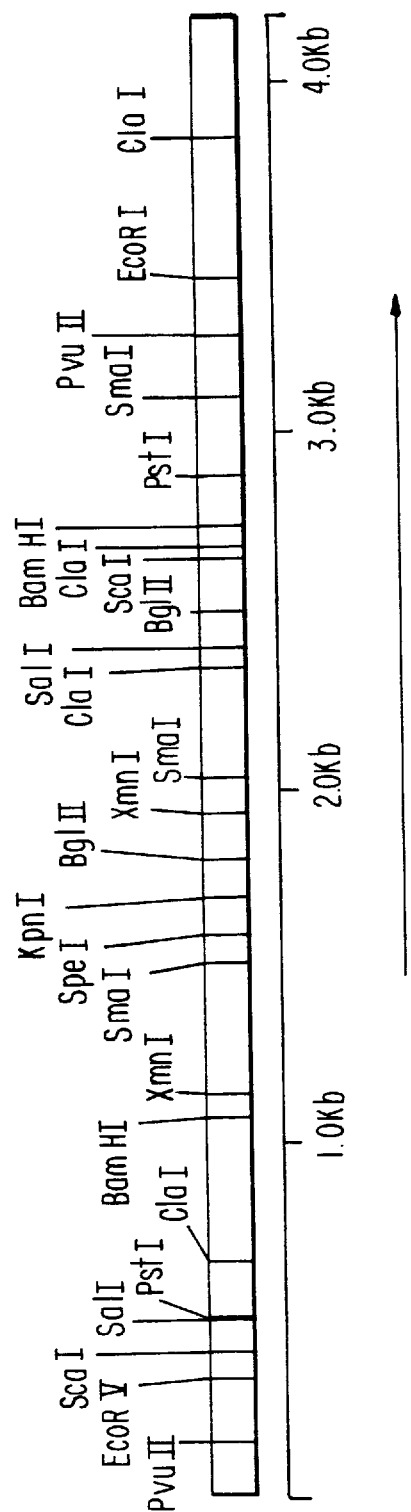
FIG. 2 shows a restriction map of a 4.2 kb genomic fragment containing an *Aspergillus oryzae* IFO 4177 5-aminolevulinic acid synthase gene.

Bacteriophage DNA from $7 \times 10^4$ plaques was transferred to duplicate circular Nytran Plus membranes (Schleicher & Schuell, Keene, N.H.) and probed with a digoxigenin (DIG)-labeled probe which was prepared by PCR amplification of *Aspergillus nidulans* hemA genomic DNA from plasmid pSE04 described in Example 2. The amplification reaction contains the following components: 1X DIG probe synthesis mix (Boehringer Mannheim, Indianapolis, Ind.), 100 μM each of dATP, dCTP, dGTP, and dTTP, 50 pmoles of primer ALAS3d and primer ALAS4e described in Example 2, 2 units of Taq DNA polymerase, and 1X Taq DNA polymerase buffer. The reaction was incubated in a Perkin-Elmer Thermal Cycler programmed for 30 cycles each at 95° C. for 1 minute, 55° C. for 1 minute, and 72° C. for 2 minutes. Denatured probe was added to the hybridization buffer at a concentration of 2 ng/ml and incubated overnight with prehybridized membranes. Prehybridization and hybridization was conducted at 42° C. in 5 X SSC, 0.1% sarkosyl, 0.02% SDS, 1% Genius blocking agent (Boehringer Mannheim, Indianapolis, Ind.), and 30% formamide. Membranes were washed twice in 5 X SSC-0.1% SDS followed by two washes in 2 X SSC-0.1% SDS. Each wash was performed for 15 minutes at room temperature. The washed membrane was exposed to Kodak X-OMAT AR film for approximately 2 hours at room temperature followed by development using a Konica QX-70 automatic film processor according to the manufacturer's instructions. Primary plaques were purified and screened a second time. Five clones were identified and excised into pZL derivatives according to the manufacturer's instructions (Bethesda Research Laboratories, Inc., Gaithersburg, Md.). The pZL derivatives were designated *E. coli* DH5α pSE11, pSE13, pSE15, pSE17, and pSE20. These clones were found to overlap and span a 4.2 kb region for which the restriction map is shown in FIG. 2.

Example 4
Southern hybridization of *Aspergillus oryzae* strain A1560 genomic DNA with a 5-aminolevulinic acid synthase (hemA) probe

*Aspergillus oryzae* strain A1560 genomic DNA (10 μg) prepared as described in Example 1 was restriction digested with either BamHI or EcoRI. The fragments were separated by electrophoresis on a 1% agarose-TBE gel. DNA was transferred to a Nytran Plus membrane in 0.4N NaOH using a TurboBlot apparatus (Schleicher & Schuell, Keene, N.H.) according to the manufacturer's instructions. The membrane was prehybridized for 2 hours at 42° C. in 5 X SSC, 0.1% sarkosyl, 0.02% SDS, 1% Genius blocking agent, and 50% formamide in a Hybaid oven (Labnet, Woodbridge, N.J.). Hybridization was accomplished with a DIG-labeled hemA probe generated by PCR amplification as described in Example 3, except the hemA clone pSE17 was used as a template with primer hemA5' 5'-TCATTTAAATGATGGAGTCTCTTCTCC-3' (SEQ ID NO:7) and primer hemA3' 5'-TCTTAATTAATCAGCTCACATGCGGG-3' (SEQ ID NO:8). DIG-labeled hemA probe (1 ng probe/ml of solution) was added to fresh hybridization buffer and incubated with the membrane overnight at 42° C. Subsequently, the membrane was washed twice for 15 minutes each at room temperature in 5 X SSC-0.1% SDS followed by two washes under the same conditions in 2 X SSC-0.1% SDS. The washed membrane was exposed to Kodak X-OMAT AR film for approximately 2 hours at room temperature followed by development using a Konica QX-70 automatic film processor according to the manufacturer's instructions.

Southern blot hybridization of *Aspergillus oryzae* genomic DNA with the *Aspergillus oryzae* hemA probe showed hybridization signals consistent with a single gene copy number. A 1.7 kb band observed in the BamHI lane was predicted from the restriction map (FIG. 2).

Example 5
Characterization of *Aspergillus oryzae* A1560 5-aminolevulinic acid synthase (hemA) gene

*E. coli* DH5α pSE17 described in Example 3 was subjected to DNA sequencing according to the following procedure. DNA sequencing was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38:47–60) using the M13 reverse (−48) and M13 forward (−20) primers (New England Biolabs, Beverly, Mass.) and primers unique to the DNA being sequenced.

The nucleotide sequence of the cloned gene reveals an open reading frame of 1911 nucleotides as shown in FIG. 3 (SEQ ID NO: 1). The coding sequence does not contain any introns which was confirmed by cDNA cloning and sequence analysis. This is in contrast to the *Aspergillus nidulans* hemA gene which contains one intron at its 5' end (Bradshaw et al., 1993, *Current Genetics* 23:501–507).

The deduced amino acid sequence of the *Aspergillus oryzae* strain A1560 gene product is shown in FIG. 3 (SEQ ID NO:2). The nucleotide sequence encodes a predicted protein of 636 amino acids with molecular weight of 68 kDa. Since this enzyme is located in the mitochondria, the N-terminus is predicted to contain a mitochondrial leader sequence. In fact, the first 35 amino acids are rich in serine, threonine, lysine, and arginine residues consistent with a function as a mitochondrial leader.

Example 6
Generation of a genomic porphobilinogen synthase gene (hemB) probe by PCR Degenerate PCR primers were designed based on the amino acid sequence flanking a 126 bp hemB fragment from *Aspergillus oryzae* (Jesper Vind, 1994, Ph.D. Dissertation, University of Copenhagen, Copenhagen, Denmark) and the homologous regions of yeast and human hemB clones (Myers et al., 1987, *Journal of Biological Chemistry* 262:16822–16829; Wetmur et al., 1986, *Proceedings of the National Academy of Sciences USA* 83:7703–7707). The oligonucleotide primers were synthesized using an Applied Biosystems Model 394 DNA/RNA Synthesizer. Sense and antisense primers shown below were used to PCR amplify the hemB fragment using pJVi60 (Vind, 1994, supra) as a template.

Sense: 5'-GT(AGCT)GC(AGCT)CC(AGCT)(AT)(CG)(AGCT)GA(CT)ATGATGGA-3' (SEQ ID NO:9)
Antisense: 5'-GC(AG)TC(AGCT)CG/T(AG)AA(AGCT)CC(AG)TA-3' (SEQ ID NO:10)

Figure 4:
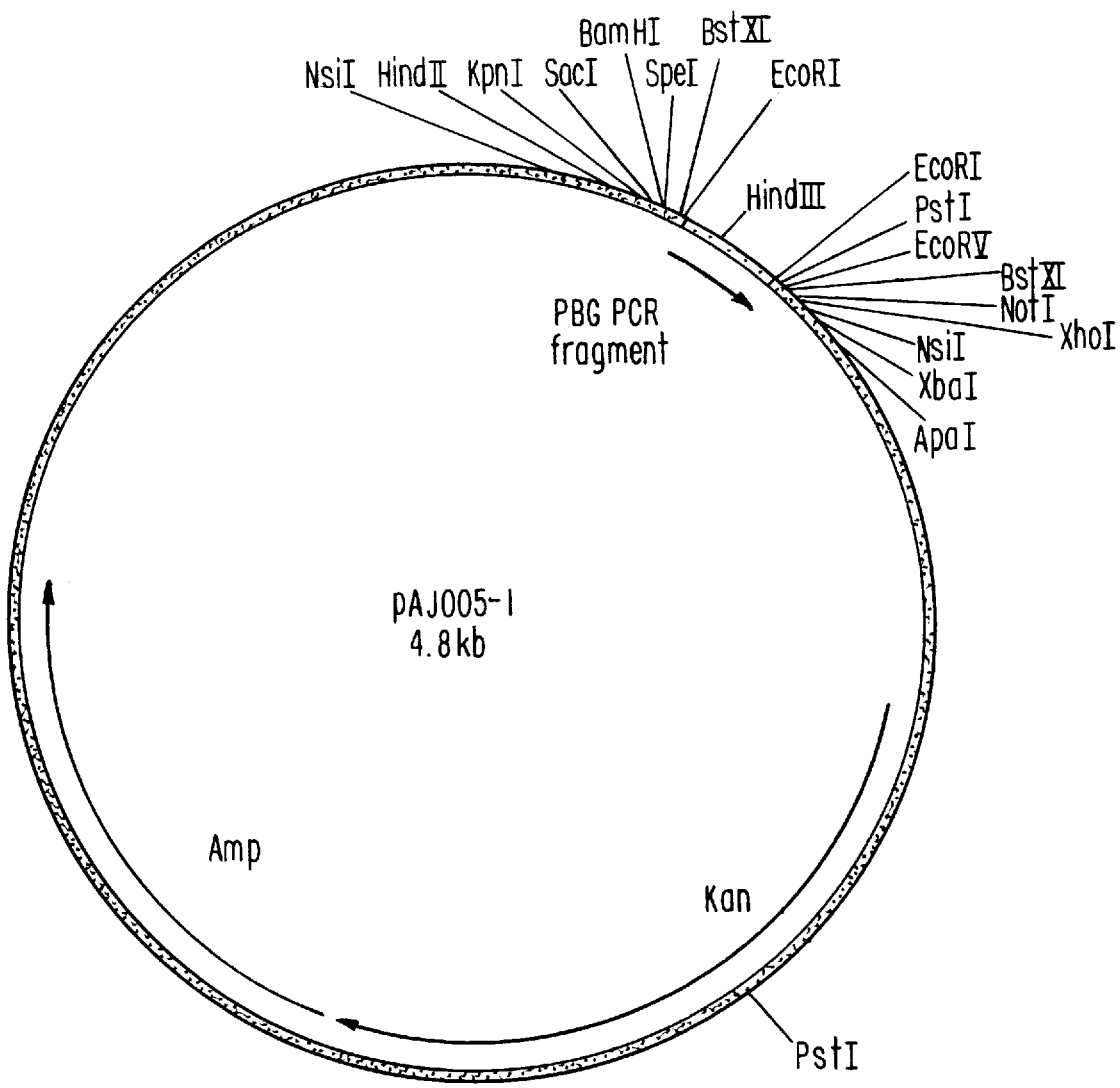
FIG. 4 shows a restriction map of plasmid pAJ005-1.

The PCR reaction (50 μl) was comprised of 10 mM Tris-HCI pH 8.3, 50 mM KCl, 1.5 mM $MgCl_2$, 0.01% w/v gelatin, 200 μM each of dATP, dCTP, dGTP, and dTTP, 500 ng of pJVi60, and 50 pmol of each PCR primer described above. The reaction was incubated at 95° C. for 3 minutes and cooled to 80° C. Then 5 units of Taq polymerase were added. The reaction was incubated in a Perkin-Elmer 9600 Thermal Cycler programmed for 35 cycles each at 95° C. for 30 seconds, 45° C. for 1 minute, and 72° C. for 1 minute. Following the last cycle the reaction was incubated at 72° C. for 5 minutes. A predicted 126 bp hemB PCR product was cloned into a pCRII vector to produce plasmid pAJ005-1 (FIG. 4).

Example 7
*Aspergillus oryzae* strain A1560 DNA libraries and identification of porphobilinogen synthase (hemB) clones

*Aspergillus oryzae* strain A1560 genomic DNA libraries were constructed as described in Example 3.

Bacteriophage DNA from $8 \times 10^4$ plaques was transferred to duplicate circular Nytran Plus membranes (Schleicher & Schuell, Keene, N.H.) and probed with a $^{32}$P-labeled PCR product derived by amplifying the hemB fragment of pAJ005-1 (see Example 6) according to Mertz and Rashtchian (1994, *Analytical Biochemistry* 221:160–165). The amplification reaction (50 μl) contains the following components: 10 mM Tris-HCl pH 8.3, 50 mM KCl, 1.5 mM $MgCl_2$, 0.01% (w/v) gelatin, 0.04 mM each of dATP, dCTP, dGTP, and dTTP, 5 μl of $^{32}$P-dCTP (3000 Ci/mmole, 3.3 μM; Amersham, Arlington Heights, Ill.), and 50 pmole each of sense primer 5'-GTGGCTCCGAGTGATAT-3' (SEQ ID NO:11) and antisense primer 5'-GCATCGCGAAAAGGACCG-3' (SEQ ID NO:12). The reaction was heated to 95 ° C. for 3 minutes followed by the addition of 5 units of Taq polymerase. The reaction was then incubated in a Perkin-Elmer Thermal Cycler programmed for 30 cycles, each cycle at 95° C. for 1 minute, 55° C. for 1 minute, and 72° C. for 1 minute. The reaction solution was passed through a Sephadex G50 column (Pharmacia, Alameda, Calif.) to remove unincorporated nucleotides and then denatured and added to the hybridization buffer. Denatured probe ($10^6$ cpm/ml) was added to hybridization buffer and incubated overnight with prehybridized membranes. Prehybridization and hybridization was conducted at 42° C. in 5 X SSC, 50 mM sodium phosphate pH 7, 5 X Denhardt's solution, 0.1% (w/v) SDS, 5 mM EDTA pH 8, 10 μg/mL denatured salmon sperm DNA, and 50% formamide. Membranes were washed four times in 0.1 X SSC, 0.1% SDS for 15 minutes at 42° C. Primary plaques that give a positive signal were screened a second time and purified according to the manufacturer's instructions. Ten genomic clones that produce a positive signal were excised from the λZipLox vector as pZL derivatives according to the manufacturer's instructions (Bethesda Research Laboratories, Inc., Bethesda, Md.) and sequenced according to the method of Hattori and Sakaki (1986, *Analytical Biochemistry* 152:232–237). The pZL derivatives were designated pAJ007-1 through pAJ007-10. Clone *E. coli* DH5α pAJ007-6 contains a 3.7 kb genomic fragment based on restriction mapping and was further analyzed.

Example 8
Characterization of the porphobilinogen synthase (hemB) gene

*E. coli* DH5α pAJ007-6 described in Example 7 was subjected to DNA sequencing according to the procedure described in Example 7.

Figure 5B:
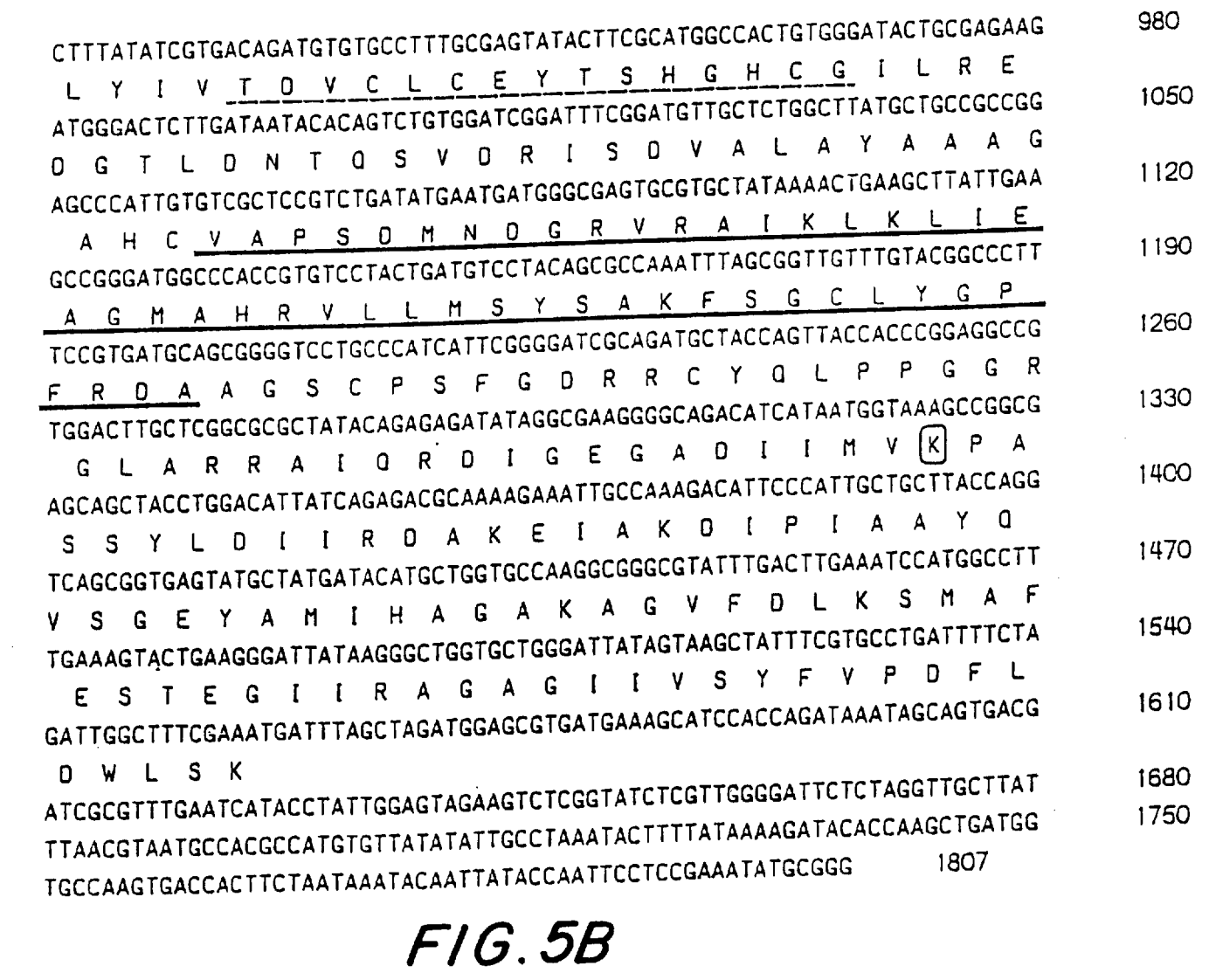

The nucleotide sequence of the cloned *Aspergillus oryzae* A1560 hemB gene reveals an open reading frame of 1308 nucleotides as shown in FIG. 5 (SEQ ID NO:3) encoding a 374 amino acid polypeptide with a predicted molecular weight of 40 kDa as shown in FIG. 5 (SEQ ID NO:4). The nucleotide sequence contains one 48 bp putative intron which was flanked by splice site consensus sequences and contains an internal consensus sequence as predicted by (Unkles, 1992, in *Applied Molecular Genetics of Filamentous Fungi*, Chapter 2, J. R. Kinghorn and G. Turner, editors, Blackie Academic and Professional Publications). The 3' splice site (TAG) was located 254 bp downstream of the Met, a 5' splice site (GTCCGC) was located 46 bp upstream of the 3' splice site, and the internal consensus sequence (TCTAAC) was located 30 bp downstream of the 5' splice site. The 5' untranslated region contains two CAAT motifs at positions −377 and −233 and may play an important role in transcriptional regulation (Gurr et al., 1987, In Kinghorn, J. R. (ed.), *Gene Structure in Eukaryotic Microbes, pp.* 93–139, IRL Press, Oxford). In addition, several putative TATA like boxes were found in the 3' untranslated region (−117, −208, −650). As expected, hemB does not appear to contain a leader sequence at the N-terminus since it was cytoplasmic in other organisms except plants (Bottemley and Muller-Eberhard, 1988, *Seminars in Hematology* 25:282–302).

Example 9
Construction of pSE52 to contain a hemAΔ::pyrG allele

Figure 6:
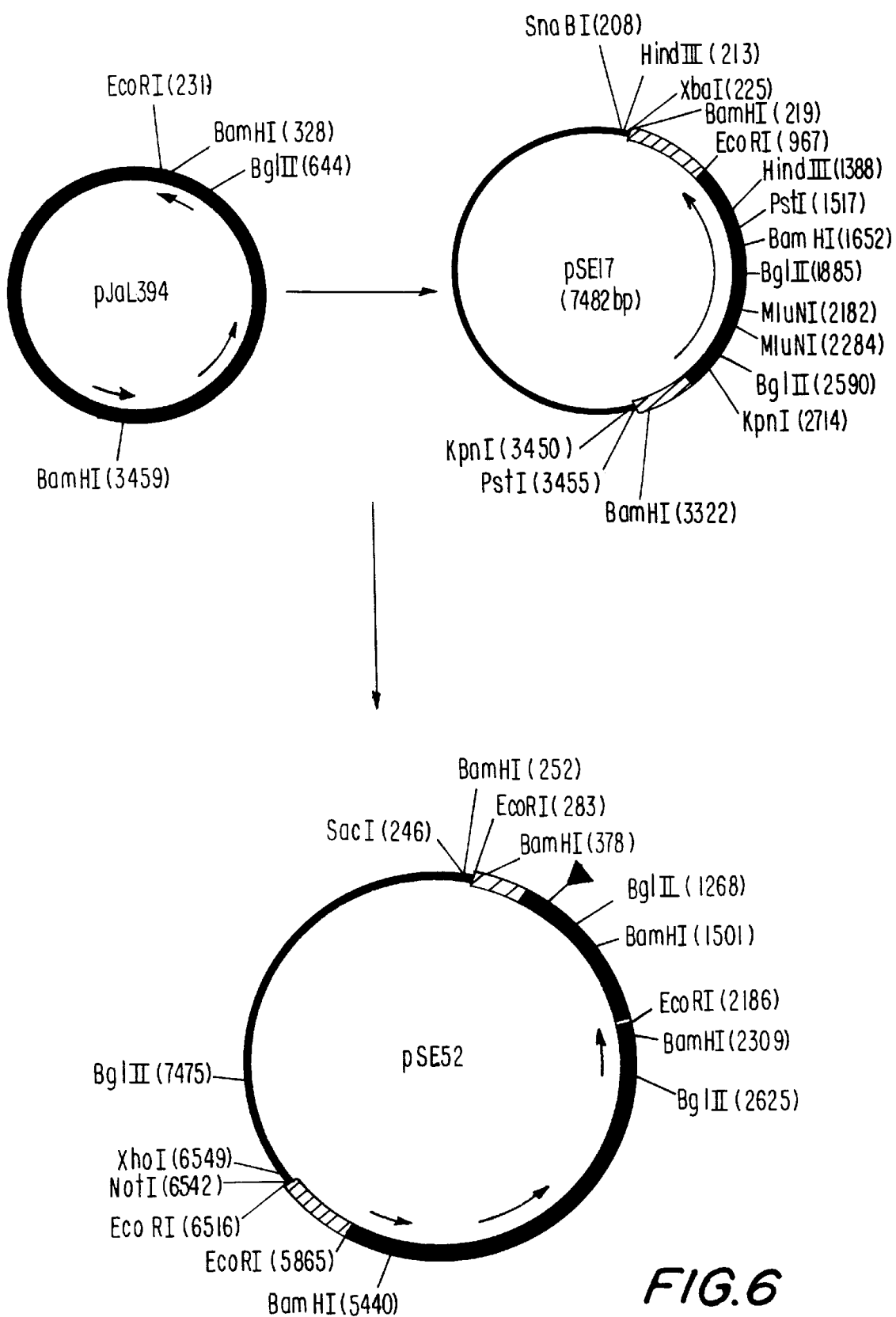
FIG. 6 shows the construction of pSE52.

Plasmid pSE52 was constructed as shown in FIG. 6 to contain a hemAΔ::pyrG allele. Specifically, a 4.1 kb fragment containing the Aspergillus oryzae pyrG gene and both 5' and 3' flanking DNA, including direct repeats designed to facilitate recombination and removal of the pyrG marker, was PCR amplified from pJaL394 using the Expand PCR kit (Boehringer Mannheim, Indianapolis, Ind.) according to the manufacturer's instructions and primers hemAdel.A and hemAdel.B shown below.

hemAdel.A:5'-ATCCATTGAAGCATCCAGGGTTAT-TGTCTC-3' (SEQ ID NO:13)

hemBdel.A: 5'-GGATTGACGAAGCAGAGGATGAC-GATGAGC-3' (SEQ ID NO:14)

The Expand PCR amplification was conducted in a Perkin Elmer GeneAmp PCR System 9600 programmed for 1 cycle at 94° C. for 2 minutes, 62° C. for 30 sceonds, and 68° C. for 3 minutes; 10 cycles at 94° C. for 15 seconds, 62° C. for 30 seconds, and 68° C. for 3 minutes with 30 second increases after each cycle; 15 cycles at 94° C. for 15 seconds, 62° C. for 30 seconds, and 72° C. for 5 minutes; and a sock cycle at 4° C.

Figure 7:
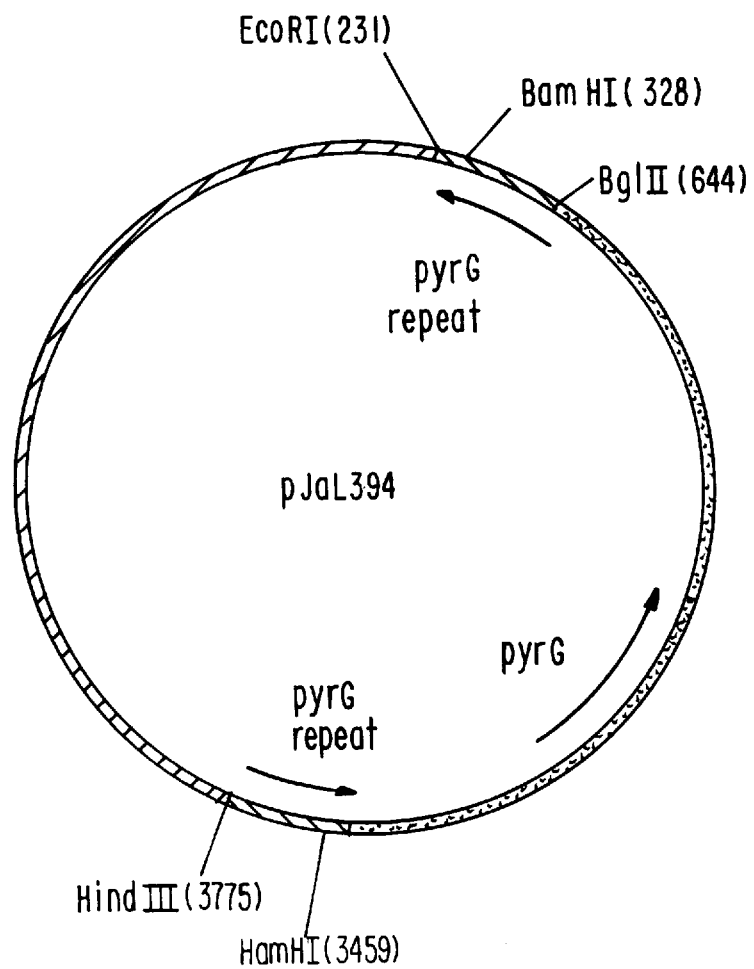
FIG. 7 shows a restriction map of plasmid pJaL394.

The product was cloned into pCRII (Invitrogen, San Diego, Calif.) according to the manufacturer's instructions to yield pSE40 and the nucleotide sequence of the open reading frame (ORF) was confirmed in two independent clones. The EcoRI fragment of pSE40 containing the pyrG gene was ligated into the EcoRI site of pSE17, which placed the pyrG gene in the 3' flanking sequence of the hemA gene to produce pSE41. pSE41 was restricted with blunt-cutting enzymes MluNI and Eco47III (to drop out a 445 bp fragment of the hemA ORF), gel purified, and re-ligated to create plasmid pSE48b. The region of the hemA gene containing the deletion was sequenced to confirm the nature of the hemAΔ::pyrG allele. Sequencing revealed as shown in FIG. 7 that the hemA deletion removed coding sequence and destroyed the reading frame of the gene (SEQ ID NOS:15 and 16). This allele was PCR amplified from pSE48b using the Expand PCR kit according to the manufacturer's instructions and primers SE48up and SE48dwn shown below using the same conditions described above:

SE48up: 5'-AATGGTCAAAACTGGCTCCTAC-3' (SEQ ID NO:17)

SE48dwn: 5'-TGTACCTGTTCTTGGGCTGTC-3' (SEQ ID NO: 18)

The PCR amplified fragment was then subcloned into pCR2.1 (Invitrogen, San Diego, Calif.) to produce pSE52 to facilitate isolation of a 6.3 kb fragment containing the hemAΔ::pyrG allele with the restriction endonucleases SacI and NotI. The 6.3 kb SacI-NotI fragment contained approximately 700 bp of both 5' and 3' flanking DNA with which to promote homologous recombination with the genomic copy of the hemA gene.

Example 10

Transformation of *Aspergillus oryzae* with hemAΔ::pyrG allele fragment

*Aspergillus oryzae* HowB425 was transformed with approximately 20 μg of the SacI-NotI 6.3 kb hemAΔ::pyrG fragment in order to replace the wild type hemA gene with the hemAΔ::pyrG deletion allele. The transformation was conducted with protoplasts at a concentration of 2–10$^7$ protoplasts per ml. One hundred μl of protoplasts were incubated at 34° C. with 10 μg DNA and 200 μl of 60% PEG 4000-10 mM HEPES-10 mM CaCl$_2$ solution for 30 minutes. Three ml of SPTC (40% PEG 4000, 0.8M sorbitol, 0.05M Tris pH 8.0, 0.05M CaCl$_2$) were added and the protoplasts were plated directly onto onto Minimal medium supplemented with either 2.5 mM or 5 mM 5-aminolevulinic acid. 5-Aminolevulinic acid auxotrophy was determined by assessing growth at 34° C. of the primary transformants grown on Minimal medium lacking 5-aminolevulinic acid. Strains whose growth under these conditions were judged to be marginal were streaked for single colony isolation. The purified single colony isolates were then subjected to a secondary 5-aminolevulinic acid auxotrophy screen using the same conditions as described for the primary screen.

Transformation of *Aspergillus oryzae* HowB425 with the deletion allele resulted in 265 colonies. Screening of 240 primary transformants on Minimal medium lacking 5-aminolevulinic acid resulted in 15 strains whose growth appeared marginal. Eleven of these strains showed very poor growth on Minimal medium in a secondary screen and 6 strains, SE29-70, 29-86, 29-87, 29-180, 29-192 and 29-197, were chosen for further single colony purification and Southern analysis.

Genomic DNA (10 μg) from each of the six transformants was prepared as described in Example 1 and restriction digested with BamHI. The fragments were separated by electrophoresis on a 1% agarose-TBE gel. DNA was transferred to a HybondN (Amersham, Arlington Heights, Ill.) nylon membrane in 0.4N NaOH using a TurboBlot apparatus (Schleicher & Schuell, Keene, N.H.) according to the manufacturer's instructions. The membrane was prehybridized for 2 hours at 42° C. in 5 X SSC, 0.1% sarkosyl, 0.02% SDS, 1% Genius blocking agent, and 50% formamide in a Hybaid oven (Labnet, Woodbridge, N.J.). The probe was prepared by PCR amplification of pSE17 using primers hemAdelup1 and hemAdeldwn1 shown below.

hemAdelup1: 5'-AGGCCTCTTGGGTTATGAATG-3' (SEQ ID NO:19)

hemAdeldwn1: 5'-TGACCTGGAGATTAGACATAG-3' (SEQ ID NO:20)

The amplification reaction (100 μl) contained the following components: 1 μg of pSE17, 50 pmol of hemAdelup1primer, 50 pmol of hemAdeldwn1 primer, 200 μM each of dATP, dCTP, dGTP, and dTTP, 1xTaq polymerase buffer (Perkin-Elmer Corp., Branchburg, N.J.), and 5 Units of Taq polymerase (Perkin-Elmer Corp., Branchburg, N.J.). The reaction was incubated in a Perkin-Elmer Model 480 Thermal Cycler programmed as follows: Cycle 1—95° C. for 5 minutes, 55° C. for 2 minutes, and 72° C. for 5 minutes; Cycle 2—30°–95° C. for 1 minute; 55° C. for 1 minute, and 72° C. for 1 minute; and Soak cycle at 4° C.

The PCR product DNA was gel isolated, purified using a QiaPure column (Qiagen, Chatsworth, Calif.), ethanol precipitated and redissolved in 25 μl of TE. Aα-$^{32}$P-dCTP-labeled probe was prepared by random priming using a Prime-It II kit (Invitrogen, San Diego, Calif.) and 2.5 μl of the purified DNA according to manufacturer's instructions. The labeled probe was purified using a G50 midi column (Five Prime Three Prime, Boulder, Colo.). The purified probe (2 μl, ~1×10$^6$ cpm) was first denatured in 0.5N NaOH at 37° C. for 2 minutes then added to 10 ml of fresh hybridization solution described above. After overnight hybridization at 42° C., the membrane was washed in 2X SSC, 0.1% SDS for 10 minutes at room temperature followed by a wash in 0.2X SSC, 0.1% SDS for 10 minutes at room temperature with 2 final washes in 0.1X SSC, 0.1% SDS for 15 minutes at 68° C. The washed membrane was rinsed in 2X SSC and exposed to Kodak Xomat AR film. Southern analysis of these strains showed that 5 contained only the hemAΔ::pyrG allele and 1 contained both wild type and hemAΔ::pyrG alleles. Two rounds of spore purification of strains SE29-70, 29-87 and 29-197 yielded isolates that failed to grow on Minimal medium demonstrating the 5-aminolevulinic acid auxotrophy.

Example 11

Rescue of the lethal hemA deletion phenotype by supplementation with 5-aminolevulinic acid or hemin The ability of either 5-aminolevulinic acid or hemin to rescue the hemA deletion phenotype was determined by supplementation of growth medium.

A 250 mM stock solution of 5-aminolevulinic acid (Porphyrin Products, Logan Utah) was prepared in water, 0.22 micron filter sterilized, stored at −20° C. in the dark, and added to prepared media immediately prior to use or pouring. 5-Aminolevulinic acid, ranging in concentration from 0.005 mg/ml to 0.3 mg/ml, was added to Minimal medium agar or YEG liquid medium (5 g of yeast extract and 20 g of glucose per liter).

A 10 mg/ml stock solution of hemin was prepared fresh in 50 mM NaOH, 0.22 micron filter sterilized, and stored on ice until use. Hemin, ranging in concentration from 0.05 mg/ml to 0.2 mg/ml, was added to Minimal medium agar.

The results showed that concentrations of 5-aminolevulinic acid as low as 30 μM (5.0 μg/ml) were sufficient to rescue the auxotrophic phenotype when added to Minimal medium agar. Growth in liquid YEG medium required slightly higher concentrations (up to 1 mM).

The results further showed that hemin was unable to support growth of any deletion strain tested when added to Minimal medium agar. These concentrations of hemin did not inhibit the growth of strains containing a wild type hemA gene. Alternate growth media and conditions with hemin may allow rescue of the hemA phenotype.

Example 12
Transformation with wild type hemA rescues the hemA deletion phenotype Rescue transformations were performed on protoplasts prepared from the first single colony isolation *Aspergillus oryzae* strain SE29-70.

Protoplasts of *Aspergillus oryzae* strain SE29-70 were transformed with 10 μg of either pSE17, which contained the 4.2 kb genomic hemA region, or pSE31, which contained the hemA ORF fused to the NA2-tpi promoter, according to the procedure described in Example 8 and plated onto Minimal medium lacking 5-aminolevulinic acid and incubated at 34° C. Transformed colonies were apparent after two days incubation, but there were also many smaller "abortive" colonies. True transformants could be distinguished by their larger size and ability to sporulate well after incubation for another day. Two hundred colonies were obtained with pSE17 and 299 colonies were obtained with pSE31, while only 28 colonies appeared on the "no DNA" control plates. Transformation efficiencies ranged from 20–30 transformants/μg DNA.

All colonies chosen for further analysis were found to be 5-aminolevulinic acid prototrophs. DNA was isolated from eight pSE17 transformants (designated strains SE40-1-7, 9, and 10) and Southern analysis according to the procedure described in Example 10 demonstrated that they contained at least one copy of the intact hemA gene, in addition to the hemA deletion allele. This data confirmed that the hemA deletion phenotype can be rescued by transformation with the wild type hemA gene.

DEPOSIT OF MICROORGANISMS

The following strains have been deposited according to the Budapest Treaty in the Agricultural Research Service Patent Culture Collection (NRRL), Northern Regional Research Laboratory, 1815 University Street, Peoria, Ill. 61604, USA.

| Strain | Accession Number | Deposit Date |
| --- | --- | --- |
| *E. coli* DH5α (pSE17) | NNRL B-21563 | April 22, 1996 |
| *E. coli* DH5α (pAJ007-6) | NRRL B-21564 | April 22, 1996 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent a substantially pure culture of each deposited strain. The deposits are available as required by foreign patent laws in countries wherein counterparts of the subject application, or its progeny are filed. However, it should be understood that the availability of a deposit does not constitute a license to practice the subject invention in derogation of patent rights granted by governmental action. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for producing a polypeptide, comprising:

(a) cultivating a respiratory-defective mutant of a bacterial or fungal cell, wherein the mutant cell comprises a nucleic acid construct comprising one or more first nucleic acid sequences and a second nucleic acid sequence in which the first nucleic acid sequence upon expression complements the respiratory defect and the second nucleic acid sequence encodes the polypeptide, in a culture medium under aerobic conditions suitable for expression of the first and second nucleic acid sequences; and (b) isolating the polypeptide from the cultivation medium of the mutant cell.

2. The method according to claim 1, wherein the first nucleic acid sequence encodes a protein which is a component of the electron transport chain.

3. The method according to claim 1, wherein the first nucleic acid sequence encodes an enzyme involved in the biosynthesis of ubiquinone.

4. The method according to claim 1, wherein the first nucleic acid sequence encodes an enzyme involved in the biosynthesis of flavin.

5. The method according to claim 1, wherein the first nucleic acid sequence encodes an enzyme involved in the biosynthesis of heme.

6. The method acording to claim 1, wherein the first and second nucleic acid sequences are contained on the same vector.

7. The method according to claim 1, wherein the first nucleic acid sequence is contained on a first vector and the second nucleic acid sequence is contained on a second vector.

8. The method according to claim 1, wherein the polypeptide is native or heterologous to the mutant cell.

9. The method according to claim 1, wherein the polypeptide is an enzyme, a hormone, a hormone variant, a receptor or a portion thereof, an antibody or a portion thereof, or a reporter.

10. The method according to claim 1, wherein the bacterial cell is a Bacillus, Pseudomonas, or Streptomyces cell.

11. The method according to claim 1, wherein the fungal cell is a filamentous fungal cell.

12. The method according to claim 1, wherein the fungal cell is a yeast cell.

13. The method according to claim 2, wherein the component is NADH-Q reductase.

14. The method according to claim 2, wherein the component is cytochrome reductase.

15. The method according to claim 2, wherein the component is cytochrome c.

16. The method according to claim 2, wherein the component is cytochrome oxidase.

17. The method according to claim 14, wherein the component is cytochrome b or cytochrome $c_1$.

18. The method according to claim 16, wherein the component is cytochrome a or cytochrome $a_3$.

19. The method according to claim 5, wherein the first nucleic acid sequence encodes an enzyme selected from the group consisting of 5-aminolevulinic acid synthase, porphobilinogen synthase, porphobilinogen deaminase, uroporphyrinogen synthase, uroporphyrinogen decarboxylase, coproporphyrinogen oxidase, protoporphyrinogen oxidase, ferrochelatase, glutamate-$tRNA_{glu}$ synthetase, glutamate-$tRNA_{glu}$ reductase and glutamate 1-semialdehyde aminotransferase.

20. The method according to claim 9, wherein the enzyme is an oxidoreductase, a transferase, a hydrolase, a lyase, an isomerase, or a ligase.

21. The method according to claim 20, wherein the enzyme is an aminopeptidase, amylase, carbohydrase, carboxypeptidase, catalase, cellulase, chitinase, cyclodextrin glycosyltransferase, cutinase, deoxyribonuclease, esterase, alpha-galactosidase, beta-galactosidase, glucoamylase, alpha-glucosidase, beta-glucosidase, glutaminase, haloperoxidase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

22. The method according to claim 11, wherein the filamentous fungal cell is an Acremonium, Aspergillus, Fusarium, Humicola, Myceliophthora, Mucor, Neurospora, Penicillium, Thielavia, Tolypocladium, or Trichoderma cell.

23. The method according to claim 12, wherein the yeast cell is a Candida, Kluyveromyces, Saccharomyces, Schizosaccharomyces, Pichia, or Yarrowia cell.

24. A respiratory-deficient mutant of a bacterial or filamentous fungal cell comprising a first nucleic acid sequence which comprises a modification of at least one of the genes essential to oxidative phosphorylation, wherein the mutant is respiratory-deficient compared to the cell when cultured under the same conditions.

25. The respiratory-deficient mutant according to claim 24 which is ubiquinone-deficient.

26. The respiratory-deficient mutant according to claim 24 which is flavin-deficient.

27. The respiratory-deficient mutant according to claim 24 which is heme-deficient.

28. A method for obtaining a respiratory-deficient mutant of a bacterial or filamentous fungal cell, comprising (a) introducing into the bacterial or filamentous fungal cell a nucleic acid sequence comprising a modification of at least one of the genes essential to oxidative phosphorylation, wherein the native gene is disrupted by homologous recombination of the introduced modified gene into the native gene; and (b) identifying a mutant of the cell from step (a) comprising the nucleic acid sequence, wherein the mutant is respiratory-deficient when cultured under the same conditions as the cell.

29. The method according to claim 28, wherein the respiratory-deficient mutant is a ubiquinone-deficient mutant.

30. The method according to claim 28, wherein the respiratory-deficient mutant is a flavin-deficient mutant.

31. The method according to claim 28, wherein the respiratory-deficient mutant is a heme-deficient mutant.

* * * * *

UNITED STATES PATENT AND TRADEMARK OFFICE
CERTIFICATE OF CORRECTION

PATENT NO. : 5,891,669

DATED : April 6, 1999

INVENTOR(S) : Jensen *et al.*

It is certified that error appears in the above-identified patent and that said Letters Patent is hereby corrected as shown below:

Title Page Section 73: delete "Novoalle" and insert --Novo Alle--

Signed and Sealed this

Fifteenth Day of February, 2000

Attest:

Attesting Officer

Q. TODD DICKINSON

*Commissioner of Patents and Trademarks*